(12) United States Patent
Hultgren et al.

(10) Patent No.: US 6,913,750 B2
(45) Date of Patent: Jul. 5, 2005

(54) THERAPEUTIC COMPOUNDS STRUCTURALLY-LINKED TO BACTERIAL POLYPEPTIDES

(75) Inventors: Scott J. Hultgren, Town and Country, MO (US); Solomon Langermann, Baltimore, MD (US); Frederic G. Sauer, St. Louis, MO (US)

(73) Assignees: MedImmune, Inc., Gaithersburg, MD (US); Washington University, St. Louis, MO (US)

( * ) Notice: Subject to any disclaimer, the term of this patent is extended or adjusted under 35 U.S.C. 154(b) by 2 days.

(21) Appl. No.: 10/027,350

(22) Filed: Dec. 28, 2001

(65) Prior Publication Data

US 2002/0086037 A1 Jul. 4, 2002

Related U.S. Application Data

(60) Provisional application No. 60/257,880, filed on Dec. 22, 2000.

(51) Int. Cl.$^7$ .................. A61K 39/02; A01N 63/00; A01N 65/00; G01N 33/554; C12P 21/06
(52) U.S. Cl. ............... 424/190.1; 424/93.1; 435/7.32; 435/69.1
(58) Field of Search ........................... 424/190.1, 93.1; 435/7.32, 69.1

(56) References Cited

U.S. PATENT DOCUMENTS 6,500,434 B1    12/2002   Langermann et al.

FOREIGN PATENT DOCUMENTS

| WO | WO 95/20657 | 8/1995 |
| WO | WO 01/04148 | 1/2001 |

OTHER PUBLICATIONS

Jones et al. Proc. Natl. Acad. Sci., vol. 90, pp. 8397–8401, Sep. 1993.*
Jones et al. Proc. Natl. Acad. Sci., vol. 92, pp. 2081–2085, Mar. 1995.*
Thankavel et al. Journal of Clinical Investigation, vol. 100, No. 5, pp. 1123–1126, Sep. 1997.*
Herren et al. Proc. Natl. Acad. Sci., vol. 95, pp. 6037–6042, May 1998.*
Langermann et al. Science., vol. 276, pp. 607–611, Apr. 1997.*
Sauer et al. Science., vol. 285, pp. 1058–1061, Aug. 1999.*
Kuehn et al. Science., vol. 262, pp. 1234–1241, Nov. 1993.*
Saulino et al. Proc. Natl. Acad Sci. vol. 97, pp. 9240–245, Aug. 2000.*
Sauer, et al., "Structural Basis of Chaperone Function and Pilus Biogenesis," Science, vol. 285, pp. 1058–1061 (Aug. 1999).
Barnhart, et al., "PapD–like chaperones provide the missing information for folding of pilin proteins," PNAS, vol. 97, No. 14 (Jul. 5, 2000).
Choudhury, et al., "X–ray Structure of the FimC–FimH Chaperone–Adhesin Complex from Uropathogenic *Escherichia coli*, " Science, vol. 285, pp. 1061–1066 (Aug. 13, 1999).
Langermann, et al., "Prevention of Mucosal *Escherichia coli* Infection by FimH–Adhesin–Based Systemic Vaccination," Science, vol. 276, pp. 607–611 (Apr. 25, 1997).
Joens, et al., "FimC is a periplasmic PapD–like chaperone that directs assembly of type I pili in bacteria," Proc. Nat'l. Acad. Sci. USA, vol. 90, pp. 8397–8401 (Sep. 1993).
Hung, et al., "Molecular basis of two subfamilies of immunoglobulin–like chaperones," EMBO Journal, vol. 15, No. 15, pp. 3792–3805 (1996).
Hultgren, et al., "The PapG adhesin of uropathogenic *Escherichia coli* contains separate regions for receptor binding and for the incorporation into the pilus," Proc. Nat'l. Acad. Sci, USA, vol. 86, pp. 4357–4361 (Jun. 1989).
Knight, et al., "Crystallization and preliminary X–ray diffraction studies of the FimC–FimH chaperone–adhesin complex from *Escherchia coli*," Acta Crystallographica, Section D, pp. 207–210 (1997).
Saulino, et al., "Ramifications of kinetic partitioning on usher–mediated pilus biogenesis," EMBO Journal, vol. 17, No. 8, pp. 2177–2185 (1998).
Bereneice McClentton Madison, "Structural, Antigenic and Functional Analysis of FIMH Protein in *Escherichia Coli* and *Klebsiella Pneumoniae* Type 1 Fimbriae," Univ. of Tennesse Cntr. for the Health Sciences, vol. 52/06–B, p. 2893, 159 pages (1990).
"Abstracts of the 89th Annual Meeting of the American Society for Microbiology," New Orleans, La, May 14–18, 1989.
Tewari, et al., "Neutrophil Activation by Nascent FimH Subunits of Type 1 Fimbriae Purified from the Periplasm of *Escherichia coli*, " Journal of Biological Chemistry, vol. 268, No. 4, pp. 3009–3015 (1993).

(Continued)

Primary Examiner—Rodney P Swartz
Assistant Examiner—Khatol S Shahnan-Shah
(74) Attorney, Agent, or Firm—Elliot M. Olstein; Alan J. Grant

(57) ABSTRACT

A protein construct comprising a pilus protein portion, preferably a structurally stabilized pilus-protein, and an additional, or effector, portion other than a pilus protein or chaperone and wherein said effector portion serves to stabilize the pilus protein portion and to confer a therapeutic activity, such as vaccine activity or anti-microbial or anti-cancer activity, on the protein construct is disclosed. Such effector portion commonly comprises a donor strand complementary segment capable of structurally stabilizing a pilus protein subunit and attaching the auxiliary portion to said subunit to form the pilus protein analog of the invention. Methods of using said protein constructs are also disclosed as well as the formation and use of analogs comprising fragments of a pilus protein linked to effector components to produce immunogenic and/or therapeutic activity.

25 Claims, 10 Drawing Sheets

OTHER PUBLICATIONS

Palaszynski et al, in *Modulation of the Immune Response to Vaccine Antigens*, vol. 92, pp 117–122 (1998).

Thankavel, et al., "Localization of a Domain in the FimH Adhesin of *Escherichia coli* Type 1 Fimbriae Capable of Receptor Recognition and use of a Domain–specific Antibody to Confer Protection against Experimental Urinary Tract Infection," American Society for Clinical Investigation, vol. 100, No. 5, pp. 1123–1136 (Sep. 1997).

Abraham, et al., "Conservation of the D–Mannose–adhesion protein among type 1 fimbriated members of the family Enterobacteriaceae," Nature, vol. 336 (Dec. 1988).

Abraham, et al., Protection Against *Escherichia coli*–Induced Urinary Tract Infections with Hybridoma Antibodies Directed Against Type 1 Fimbriae or Complementary D–Mannose Receptors, Infection and Immunity, vol. 48, No. 3, pp. 625–628 (Jun. 1985).

Hanley, et al., "Molecular Basis of *Escherichia coli* Colonization of the Upper Urinary Tract in BALB/c Mice," Amer. Society for Clinical Investigation, Inc., vol. 75, pp. 347–360 (Feb. 1985).

Langermann et al., J. Infectious Dis., vol. 181, pp. 774–778 (2000).

Langermann et al., J. Infectious Dis., vol. 183, Suppl., pp. S84–S86 (2001).

Dodson et al, PNAS (USA), vol. 90, pp. 3670–3674 (1993).

* cited by examiner

B

A

B

A

D

C

THERAPEUTIC COMPOUNDS STRUCTURALLY-LINKED TO BACTERIAL POLYPEPTIDES

This application claims priority of U.S. Provisional Application 60/257,880, filed 22 Dec. 2000, the disclosure of which is hereby incorporated by reference in its entirety.

FIELD OF THE INVENTION

The present invention relates generally to the field of vaccines and antibodies comprising bacterial pilus-protein polypeptides, especially pilins and adhesins utilized in the usher-chaperone pathway for pilus synthesis, wherein such proteins are attached to accessory effector structures capable of conferring or enhancing immunological or other therapeutic or prophylactic effect on said subunits.

BACKGROUND OF THE INVENTION

Protein chaperones not requiring ATP for their functioning include the Pap-D-like periplasmic chaperones found in bacteria. These proteins are able to direct formation of the appropriate three dimensional conformation in bacterial pilus and non-pilus subunits. As used herein, and unless expressly stated otherwise, the term "chaperone" means periplasmic chaperones having the distinguishing characteristics described herein.

In bacterial species, these chaperones are responsible for mediating the synthesis of large scale oligomeric structures such as pili, the adhesive fibers expressed in most bacteria of the *Enterobacteriaceae* family (e.g., *Escherichia coli*).

Pili are heteropolymeric structures that are composed of several different structural proteins required for pilus assembly. Pili, also called fimbriae or fibrillae, facilitate the adhesive qualities of bacteria that often lead to colonization and infection of various tissues of the host animal, especially on mucosal surfaces. Such adhesion is facilitated by the presence in the pilus of a protein called an "adhesin," of which FimH is an example.

Different types of pili have been recognized. Type 1 pili-carrying bacteria recognize and bind to D-mannose in glycolipids and glycoproteins of bladder epithelial cells. Proteins forming the pili have been considered good candidates for vaccines. P pili are adhesive organelles encoded by eleven genes in the pap (pilus associated with pyelonephritis) gene cluster found on the chromosome of uropathogenic strains of *E. coli*. The biogenesis of P pili and Type 1 pili occurs via the highly conserved chaperone/usher pathway. (Thanassi et al, *Curr. Op. Microbiol.* 1,223 (1998); Hung et al, EMBO J. 15, 3792 (1994).

Type 1 pili are composite fibers consisting of a short thin tip fibrillum joined to a thicker, rigid pilus rod and comprising an ordered array of homologous pilins (FimA, FimF, FimH, and FimG) with the FimH adhesin at its tip. FimH mediates binding to mannose-oligosaccharides present on mucosal surfaces and thus mediates adherence to mannosylated receptors on the bladder epithelium, which is critical to the ability of uropathogenic *Escherichia coli* to cause cystitis. (See: Langermann et al, *Science* 276, 607 (1997).

The PapD-like superfamily of periplasmic chaperones directs the assembly of over 30 diverse adhesive surface organelles that mediate the attachment of many different pathogenic bacteria to host tissues, a critical early step in the development of disease. (See Soto and Hultgren, *J. Bacteriol.* 181, 1059 (1999)) PapD, the prototypical chaperone, is necessary for the assembly of P pili (Lindberg et al, *J. Bacteriol.* 171, 6052 (1989)) whereas its homologue, called FimC, directs the assembly of type 1 pili (Jones et al, *Proc. Natl. Acad. Sci. USA* 90, 8397 (1993)).

*E. coli* is the most common pathogen of the urinary tract, accounting for greater than 85% of cases of asymptomatic bacteriuria, acute cystitis and acute pyelonephritis, as well as greater than 60% of recurrent cystitis, and at least 35% of recurrent pyelonephritis infections. Because of the high incidence, continued persistence, and significant expense associated with *E. coli* urinary tract infections, there is a need for a prophylactic vaccine to reduce susceptibility to this disease. It is widely accepted that colonization of the urinary epithelium is a required early step so that disruption or prevention of pilus-mediated attachment of *E. coli* to urinary epithelia should prevent or retard the development of urinary tract infections.

A major drawback to adhesin based vaccines of any kind has been the fact that adhesins are often only a minor component of the pilus, cannot be produced in large quantities, and therefore will tend not to elicit a particularly strong immunogenic effect. Although recombinant technology has succeeded in producing adhesin proteins in pure form, these are often rapidly proteolytically degraded when the corresponding chaperone is absent. Such adhesins are readily stabilized by the presence of periplasmic chaperone molecules (the latter also being important in proper synthesis of adhesins).

In gram negative bacteria, such as *E. coli*, between the inner and outer membrane lies the periplasmic space. Proteins destined for secretion or assembly across the outer membrane often must fold within the periplasmic space prior to their secretion and/or assembly. Chaperones are often to be found within this periplasmic space. Among the proteins found in the periplasm are the adhesin FimH and its chaperone FimC.

Thus, gram negative bacteria, including many pathogenic organisms, assemble a variety of pilus and non-pilus organelles on their surfaces by the conserved chaperone-usher pathway. Many of these organelles mediate attachment to host tissues, essential for the disease process in many bacterial infections.

Throughout this disclosure the terms pilus, pili, fimbrium, fimbriae, fibrillum and fibrilla are be used interchangeably, with incidental use of the singular or plural form of any of these terms in no way limiting the breadth of the disclosed invention.

A "periplasmic chaperone" is defined herein as a protein localized in the periplasm of bacteria that is capable of forming complexes with a variety of proteins, especially pilus-proteins, including adhesins, especially FimH (where the corresponding chaperone is FimC) via recognition of a common binding epitope (or epitopes). Such chaperones are characterized by their similarity in properties to PapD, especially by their possession of an immunoglobulin-like fold for binding to pilus-proteins, such as adhesins. Such periplasmic chaperones have an effector function, specifically targeting the subunits to outer membrane assembly sites for their incorporation into pili and are characterized in part by the presence of an immunoglobulin-like fold. Like PapD, FimC uses its immunoglobulin-like domains to recognize and bind to pilus subunit proteins, such as the adhesin FimH.

The co-ordinated assembly of pili, as well as of other complex hetero-oligomeric organelles, requires correct incorporation of individual subunits in a predefined order during biogenesis and the prevention of premature associations between the intrinsically aggregative subunits. Type 1 pilus biogenesis proceeds via a highly conserved pathway that is involved in the assembly of over 30 adhesive organelles assembled by the adhesin-usher pathway in gram-negative bacteria. [Soto & Hultgren, *J. Bacteriol.* 181, 1059 (1999)].

While the utility of adhesins as vaccines has been demonstrated, large scale production of adhesins and other pilus-derived proteins has been complicated by the requirement of a chaperone that must be co-expressed with the adhesin in order for it to properly fold and result in a stable structure. It has now been shown that polypeptides, such as adhesins, can be prepared in a pure form without the need of co-expressing the chaperone, and without the need for the chaperone, or any other protein, thereby permitting large scale production of pure adhesins, or any other pilus subunits, for use, inter alla, as vaccines. [See: U.S. provisional patent application Nos. 60/144359, filed Jul. 16, 1999, and 60/184442, filed Feb. 23, 2000, and U.S. application Ser. No. 09/615,846, filed Jul. 13, 2000, the disclosures of which are hereby incorporated by reference in their entirety].

Pilus subunits also possess an N-terminal extension, usually about 8–20 amino acids long. In the PapD-PapK structure, this N-terminal extension is disordered. It does not contribute to the fold of the subunit but instead projects away from the subunit, where it is free to interact with another subunit. Biochemical and mutagensis experiments indicate that both the subunit groove and N-terminal extensions are involved in subunit-subunit interactions. Thus, it has been proposed that during pilus assembly, via a mechanism termed "donor strand exchange," the N-terminal extension of a subunit replaces the G1 b-strand of the chaperone bound to its neighboring subunit. The mature pilus thus consists of an arrangement of subunits such that each contributes a strand to complete the Ig fold of its neighbor. The adhesin lacks this N-terminal extension (instead, having a receptor-binding domain N-terminal to its pilin domain) consistent with its position at the tip of the pilus, where it has no neighboring subunit that requires completion of an Ig fold.

Thus, the contribution of a chaperone, such as FimC or PapD, to the overall structure of a pilin, such as in the FimC-FimH complex, or in the PapD-PapK complex, was determined by solving the structure of such complexes by X-ray diffraction [see: Choudhury et al, X-ray Structure of the FimC-FimH Chaperone-Adhesin Complex from Uropathogenic *E. coli, Science* 285, 1061 (1999); Sauer et al, Structural Basis of Chaperone Function and Pilus Biogenesis, *Science* 285, 1058 (1999); Barnhart et al., PapD-like Chaperones Provide the Missing Information for Folding of Pilin Proteins, *Proc. Natl. Acad. Sci. USA,* 10, 1073/pnas.130183897 (published online Jun. 20, 2000), the disclosures of all of which references are hereby incorporated by reference in their entirety].

Such donor-strand complemented subunits as discussed in these references, especially that of Bamhart et al, as well as the structures disclosed herein, are referred to herein as "dsc-subunits," for example, as a "dsc-pilin" or "dsc-adhesin" such as "dsc-FimH" or "dsc-PapG." These dsc-subunits have a missing b-strand, for example (see FIG. 1 for domain structure of an adhesin, such as FimH), derived from the N-terminal extension of another subunit, linked to the C-terminus of said subunit, such as by a short amino acid linker. This missing b strand, when replaced by a donor strand sequence, thereby allows the dsc-subunit to fold into a native-like conformation in the absence of the chaperone. The dsc-subunits are thus stable, unlike wild type counterparts present in the periplasm. In accordance with the present invention, such stabilized subunits are linked to effector molecules, such as polypeptides, including antibodies, thereby providing highly useful therapeutic agents.

In accordance with the present invention, there are provided herein antibacterial therapeutics, comprising subunits linked to other polypeptide or non-polypeptide moieties, that limit or prevent attachment of bacterial pathogens and thus eliminate mortality and morbidity associated with such diseases.

BRIEF SUMMARY OF THE INVENTION

In one aspect, the present invention relates to a protein construct, preferably an isolated pilus protein construct, comprising a pilus protein portion linked to an effector portion. In one embodiment thereof, the present invention relates to said protein construct wherein said pilus protein portion that is linked to an effector portion comprises either a pilus protein or an active fragment thereof. The isolated pilus-protein construct of the invention does not include such natural structures as a pilus or many of the substructures formed in nature during the assembly of a pilus or natural complexes such as those formed by combination of a chaperone with a pilus-protein.

In preferred embodiments, said pilus protein comprises a pilin selected from the group consisting of FimH, FimA, FimG, FimF, PapG, PapA, PapE, PapF, and PapK or active fragments thereof.

In another aspect, the present invention relates to a protein construct wherein said pilus protein portion that is linked to an effector portion is a structurally stabilized pilus protein portion that comprises either a structurally-stabilized pilus protein or a structurally-stabilized fragment of such structurally-stabilized pilus protein.

In a preferred embodiment, said structurally-stabilized pilus-protein comprises a structurally-stabilized pilin selected from the group consisting of FimH, FimA, FimG, FimF, PapG, PapA, PapE, PapF, and PapK or an active fragment thereof.

In a preferred embodiment, the present invention relates to a protein construct wherein the structurally-stabilized pilus protein that is linked to an effector portion is a donor strand complemented (dsc)-pilus protein, especially a donor strand complemented pilin (dsc-pilin), such as where said pilin is one of FimH, FimA, FimG, FimF, PapG, PapA, PapE, PapF, and PapK, and including adhesins, such as FimH and PapG, and active fragments thereof. Such active fragments commonly comprise all or part of the stabilizing donor strand.

As already described, a pilus-protein assembled into a pilus by the usher-chaperone pathway is structurally stabilized by the insertion of a donor strand, provided by the chaperone, into the pilus-protein to replace a missing fold and structurally stabilize said pilus-protein. In separate embodiments of the present invention, a pilus-protein construct is structurally stabilized by such a donor strand provided by some additional structure other than a chaperone or another pilus protein to provide a dimeric-type of structure. The dsc-segment may be linked to said pilus protein by covalent or non-covalent means, the latter including electrostatic and hydrophobic interactions.

Thus, as used herein, a donor strand is a peptide or other moiety comprising or derived from either an N-terminal extension of a pilus subunit (or other subunit assembled by the chaperone-usher pathway) or a G1 strand of a PapD-like chaperone that completes the immunoglobulin-like fold of a another subunit by providing the missing strand to the latter subunit. A donor strand can be linked covalently or non-covalently to other moieties and can thereby serve to link said moieties to proteins to which the donor strand contributes a missing element. Of course, other structural and functional equivalents will no doubt suggest themselves to those of skill in the relevant art.

An N-terminal-subunit is a pilus subunit or other subunit assembled into its final structure by the chaperone-usher pathway whose N-terminal extension or portion thereof has be removed genetically or otherwise.

In additional and more specific embodiments, the protein construct of the invention comprises a polypeptide, including an immunoglobulin, or an adjuvant. In a preferred embodiment, the pilus-protein construct comprises at least one heavy and one light chain of an antibody, most preferably where said immunoglobulin is an antibody. In highly preferred embodiments thereof, said antibody has specificity for at least one antigenic determinant of a microorganism, especially wherein said microorganism is selected from the group consisting of viruses, bacteria, fungi and protozoans, most especially where said microorganism is a bacterium, such as where said bacterium is *Escherichia coli*. Such antibodies are often neutralizing antibodies and may include high potency antibodies. Such antibodies may include VITAXIN® and SYNAGIS® as non-limiting examples.

In another preferred embodiment, the protein construct of the invention comprises an adjuvant. In accordance with the invention, such protein constructs are the basis for potent vaccines useful in the prevention of diseases, especially urinary tract infections.

In other embodiments, the present invention relates to compositions comprising the protein constructs disclosed herein, wherein said constructs are suspended in a pharmacologically acceptable carrier.

The present invention also provides a vaccine comprising a prophylactically effective amount of the protein constructs of the invention suspended in a pharmacologically acceptable carrier.

The present invention also relates to a process for preventing or treating a disease in a human patient comprising administering to a patient at risk thereof or afflicted therewith a prophylactically or therapeutically effective amount of the vaccines according to the invention, especially wherein said disease is a urinary tract infection, most especially a urinary tract infection is caused by a bacterium, such as *Escherichia coli*.

In additional preferred embodiments, the pilus-protein constructs of the invention are constructs in which the dsc-stabilized pilus protein is any pilus protein used in nature for assembly into a pilus via the usher-chaperone pathway especially where this dsc-stabilized pilus protein is a dsc-stabilized pilin, most especially a pilin of the group FimH, FimA, FimG, FimF, PapG, PapA, PapE, PapF, and PapK, which include the adhesins FimH and PapG.

In another embodiment of the present invention, the pilus-protein constructs disclosed herein comprise an organic chemical agent, especially one that has potent therapeutic activity, most especially an antimicrobial agent or an anticancer agent.

In an additional embodiment, the present invention relates to a pilus-protein construct as described herein comprising an oligonucleotide or polynucleotide sequence, especially one in which said oligonucleotide or polynucleotide sequence is chemically linked to and provides a donor strand oligopeptide sequence for stabilizing the pilus-protein portion of the construct.

In a further embodiment, the present invention relates to pilus protein constructs comprising a fragment of a pilus protein, such as a mannose-binding fragment, and an auxiliary component linked to said fragment and wherein said auxiliary component is a polypeptide, including an immunoglobulin, or an adjuvant or a polypeptide or some immunogenic structure conferring vaccine activity on said construct.

BRIEF DESCRIPTION OF THE DRAWINGS

FIG. 3. Examples of dsc subunits. A. A dsc subunit whose donor strand is covalently linked to the subunit. B. A dsc adhesin whose donor strand is covalently linked to the subunit. The linker is shown as a thick gray line. The donor strand that completes the subunit fold is shown as a black arrow between the A and F strands of the subunit. C. A dsc subunit whose donor strand is non-covalently linked to the subunit. D. A dsc adhesin whose donor strand is non-covalently linked to the subunit.

FIG. 4. General scheme of a portion of the invention—donor-strand linkage of molecules to subunits. An additional effector component (represented as a labeled box) is linked to a subunit via a donor strand. The additional effector component is any moiety that confers a desirable property to or enhances a desirable property of the resulting molecule. A. An additional effector component joined to a subunit via a covalently-linked donor strand. B. An additional effector component joined to an adhesin via a covalently-linked donor strand. C. An additional effector component joined to a subunit via a non-covalently-linked donor strand. D. An additional effector component joined to an adhesin via a non-covalently-linked donor strand.

DETAILED DESCRIPTION OF THE INVENTION

Figure 1:
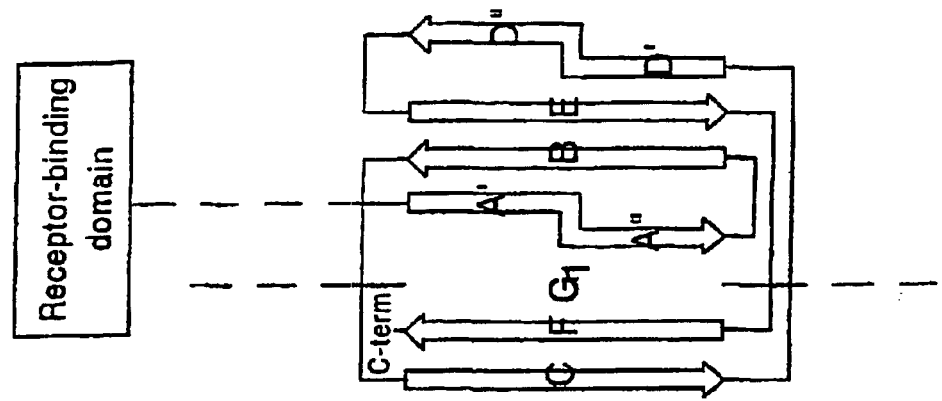
FIG. 1. Donor strand complementation of subunits. A. A subunit with an N-terminal extension. B. An adhesin. The six strands of the pilin fold are indicated as white arrows and labeled A–F. The A and D strands are subdivided into A' and A" and D' and D" portions, respectively. The C-terminus of the subunit (C-term) is indicated. The N-terminal extension is indicated as a black arrow and the receptor-binding domain as a labeled box. The G1 strand of the chaperone that participates in donor strand complementation is indicated as a gray arrow. The dotted lines at either end of this arrow indicate additional protein not shown.
Figure 1:
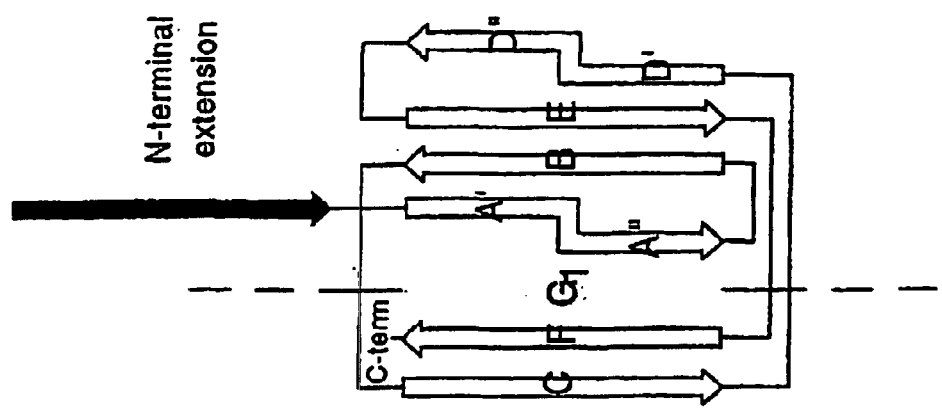
Figure 2:
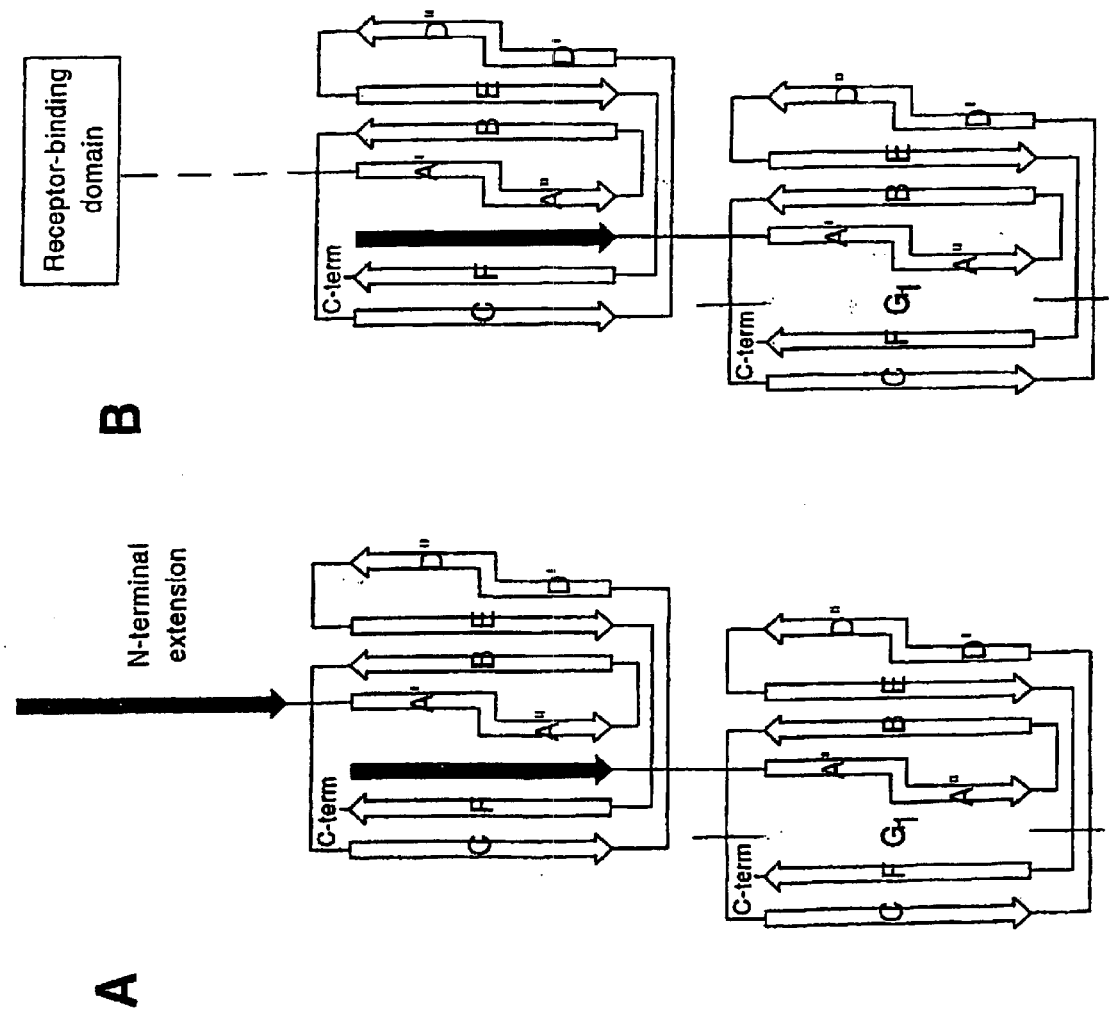
FIG. 2. Subunit—subunit interactions after donor strand exchange. A. Two subunits. B. An adhesin and another subunit. The labeling and color-coding are as in FIG. 1. In each diagram, the N-terminal extension of the lower subunit now completes the fold of the upper subunit. The lower subunit in each case remains donor strand complemented with the G1 strand of the chaperone until the next incoming subunit is incorporated.
Figure 3A:
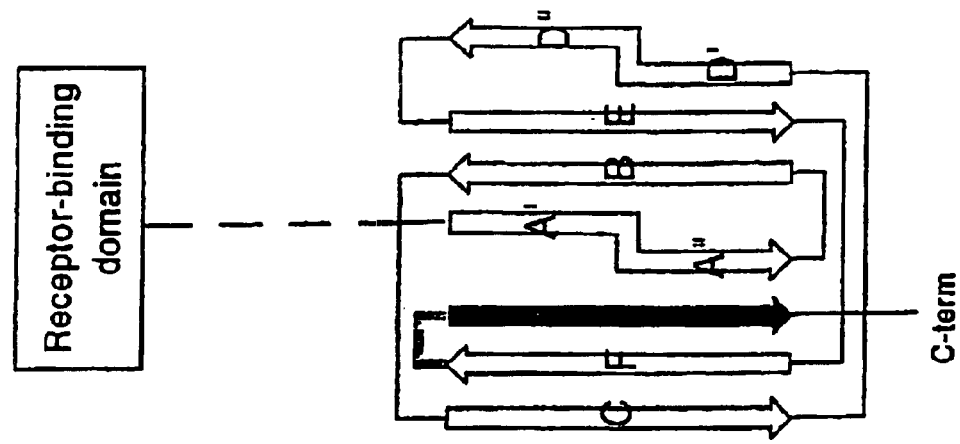
FIGS. 3A and 3B follow in sequence.
Figure 3A:
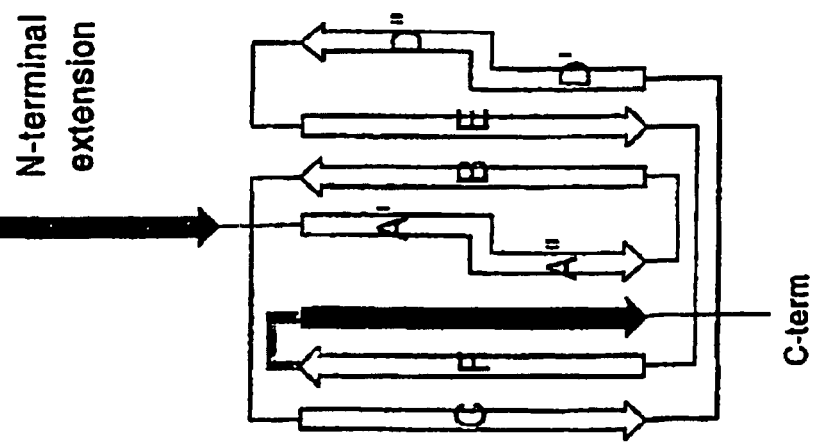
Figure 3B:
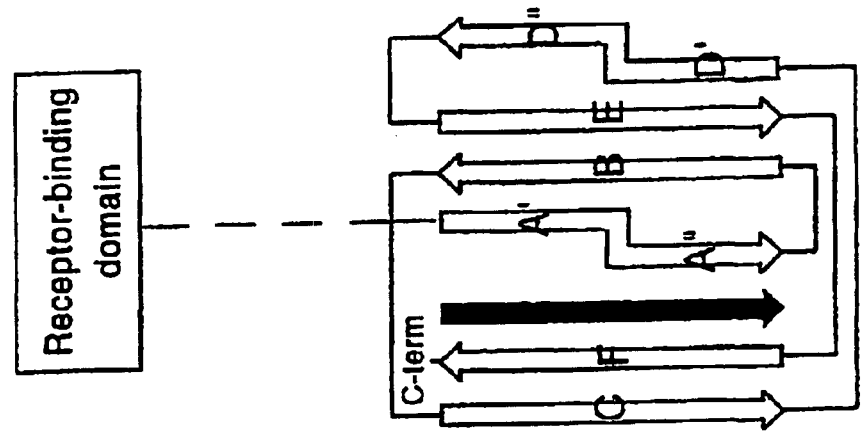
Figure 3B:
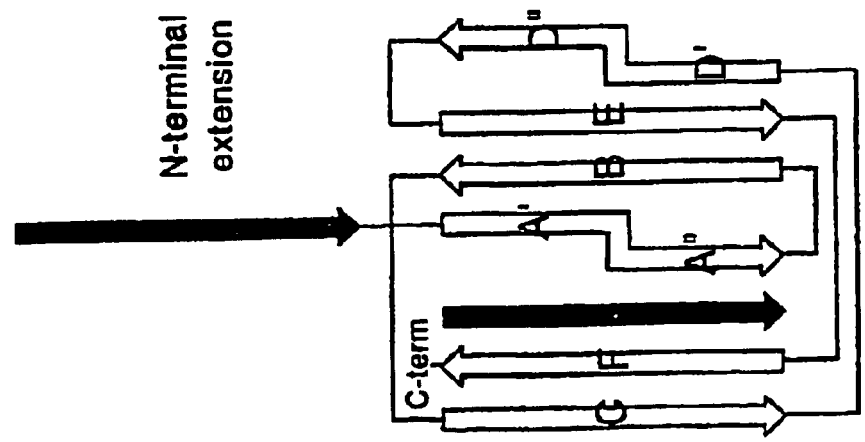
Figure 4A:
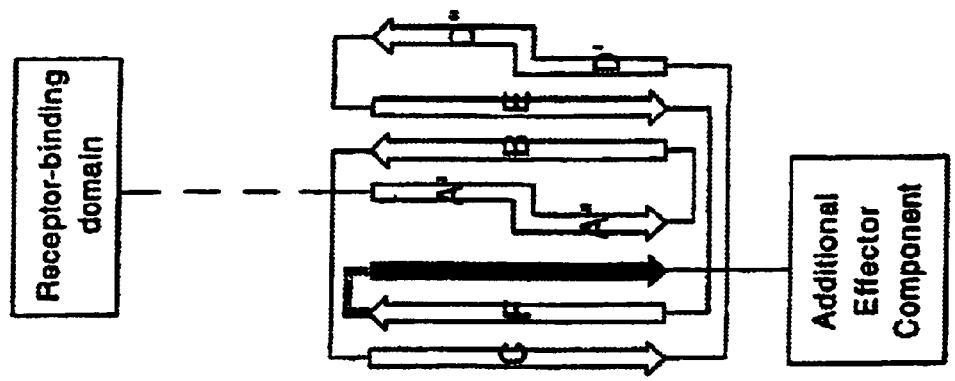
FIGS. 4A and 4B follow in sequence.
Figure 4A:
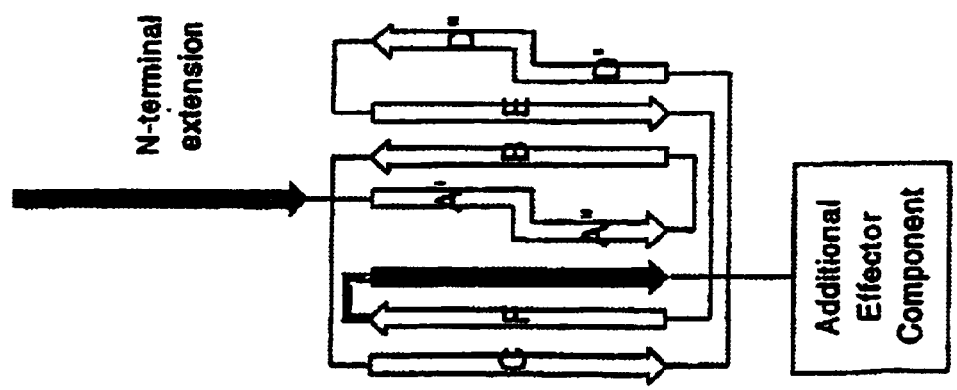
Figure 4B:
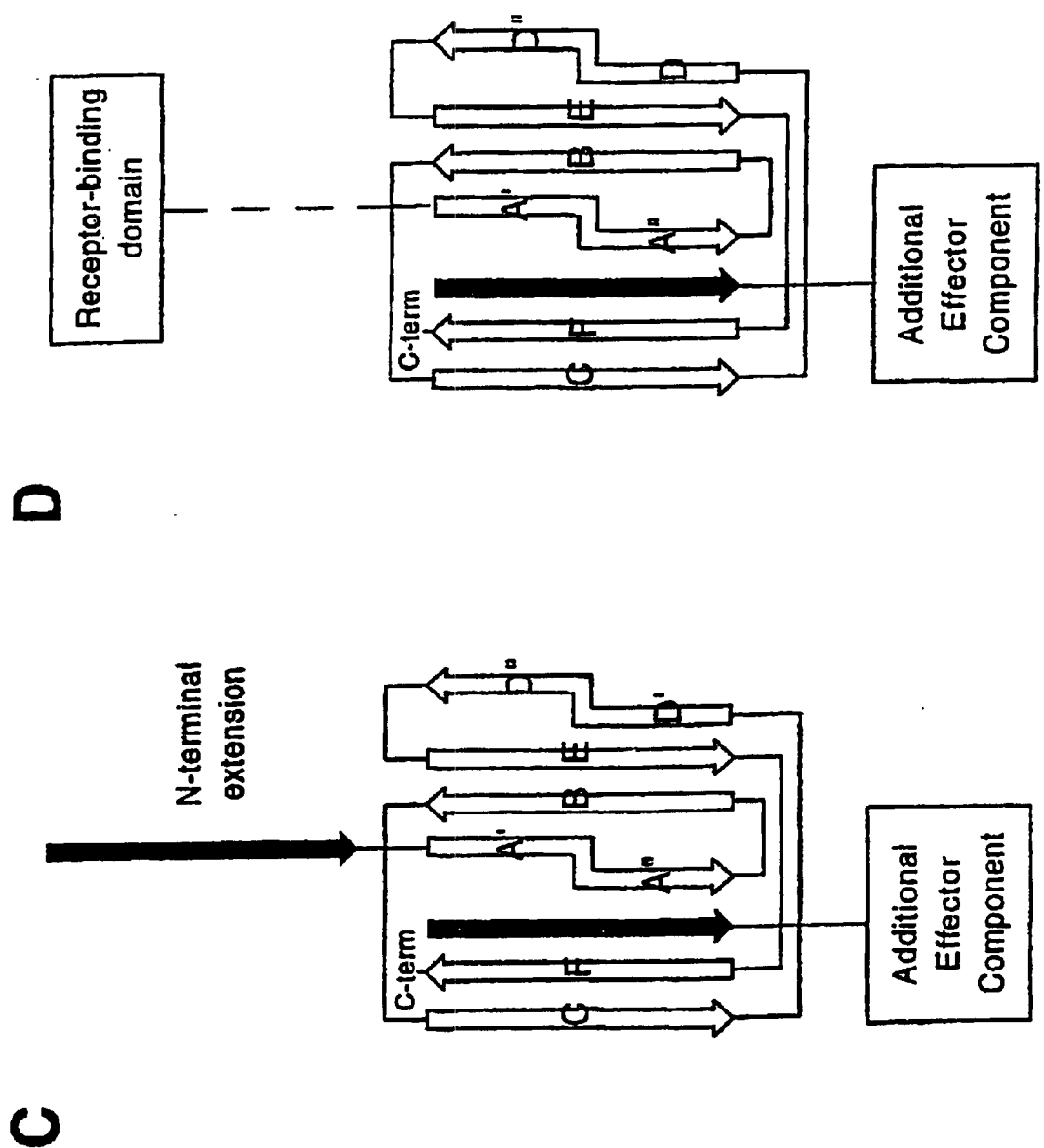
Figure 5:
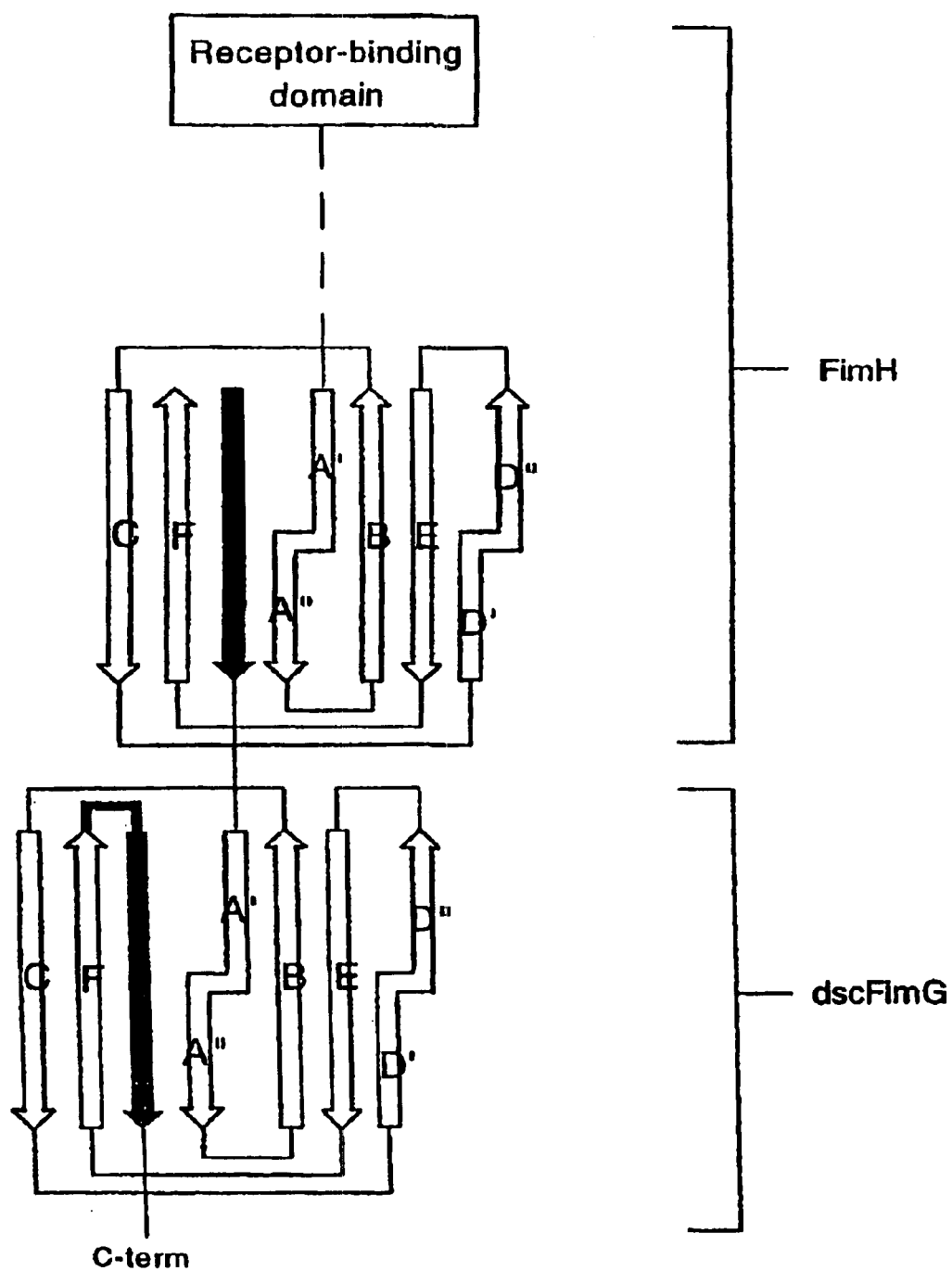
FIG. 5. An example of the invention—FimH-dscFimG. The N-terminal extension of dscFimG (black arrow) completes the fold of FimH, thus linking the two molecules non-covalently. The donor strand of FimF (gray arrow) completes the fold of FimG in the dscFimG portion. The FimH-dscFimG is potentially useful as a vaccine.
Figure 6:
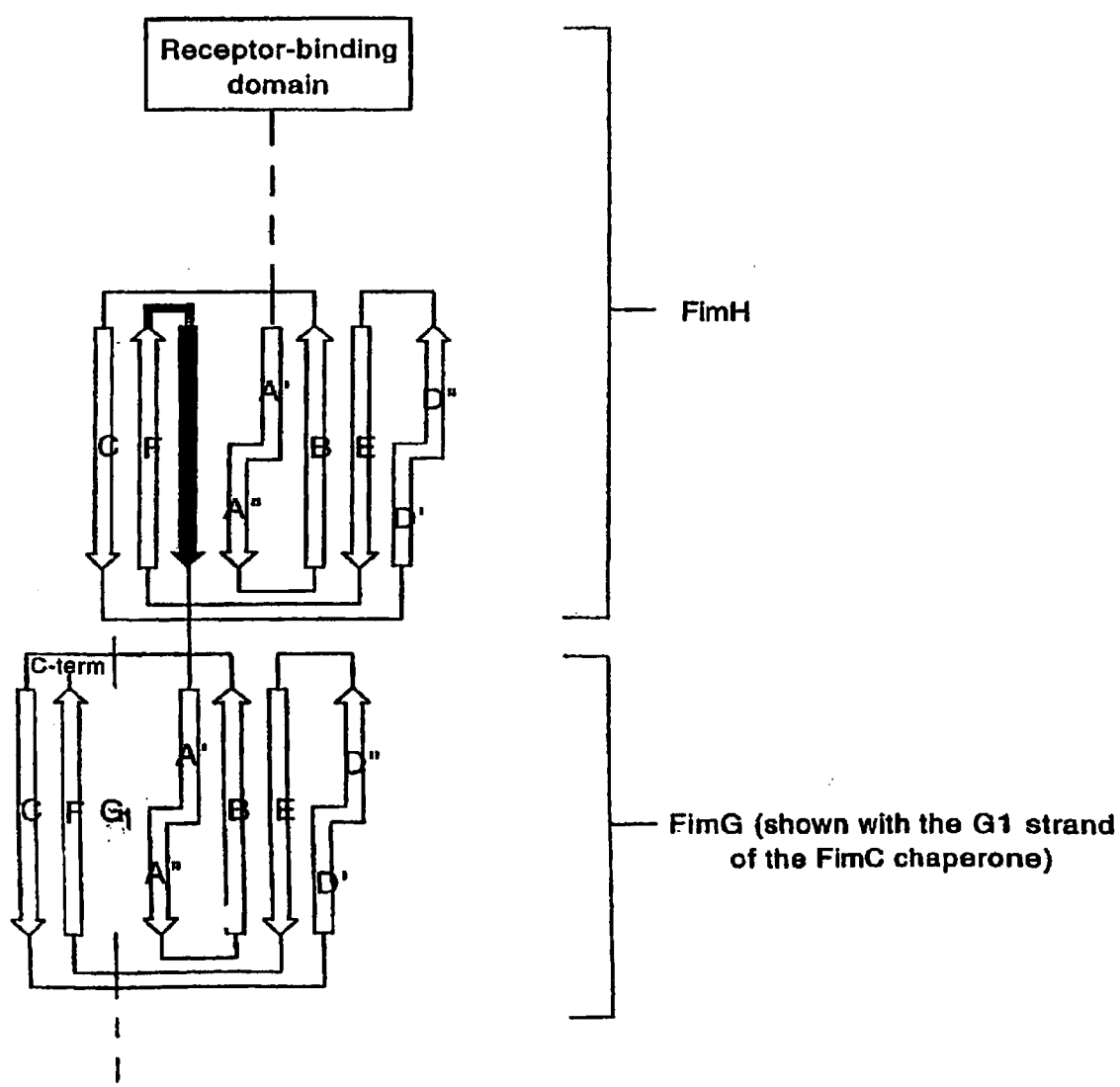
FIG. 6. An example of the invention—FimH covalently linked to FimG. The linker (in this case, four amino acids) is shown as a thick gray line. The fold of the FimG portion is completed by the G1 strand of the FimC chaperone (gray arrow). Coexpression of FimC with the covalently-linked FimG-FimH molecule produces a stable heterodimeric complex of the two molecules.

In one aspect, the present invention relates generally to the field of polypeptides, including immunogenic polypeptide structures capable of acting as vaccines, and also to structurally stabilized proteins, such as pilins and pilus subunits, especially adhesins, derived from bacteria, especially *Escherichia coli,* and to antibodies generated thereto. In accordance with the present invention such proteins serve to stabilize multimeric vaccine polypeptides as well as to target therapeutically active antibodies to sites of infection.

In its most general aspect, the present invention relates to a protein construct, especially an isolated or purified protein construct, comprising a pilus protein portion linked to an effector portion. Said protein constructs do not include a pilus, naturally occurring intermediates of pili formed during assembly of such structures or complexes formed between a pilus-protein and a periplasmic chaperone. Thus, the present invention relates to an isolated protein construct comprising a pilus protein portion linked to an effector portion wherein said pilus protein portion comprises a single pilus protein, including active fragments thereof, wherein said pilus protein portion is not attached to a bacterial cell and wherein said effector portion does not comprise all or part of either a bacterial pilus-protein or bacterial chaperone.

In one embodiment, the present invention relates to such a protein construct wherein said pilus protein portion that is linked to an effector portion comprises an active fragment of a pilus protein, including an N-terminal deleted pilus protein.

Pilus subunits also possess an N-terminal extension, usually about 8–20 amino acids long. In the PapD-PapK structure, this N-terminal extension is disordered. It does not contribute to the fold of the subunit but instead projects away from the subunit, where it is free to interact with another subunit. Biochemical and mutagensis experiments indicate that both the subunit groove and N-terminal extensions are involved in subunit-subunit interactions. Thus, it has been proposed that during pilus assembly, via a mechanism termed "donor strand exchange," the N-terminal extension of a subunit replaces the G1 b-strand of the chaperone bound to its neighboring subunit. The mature pilus thus consists of an arrangement of subunits such that each contributes a strand to complete the Ig fold of its neighbor. The adhesin lacks this N-terminal extension (instead, having a receptor-binding domain N-terminal to its pilin domain) consistent with its position at the tip of the pilus, where it has no neighboring subunit that requires completion of an Ig fold.

In accordance with the foregoing, the present invention also relates to a protein construct comprising a structurally stabilized pilus protein portion linked to an effector portion wherein said structurally-stabilized pilus-protein portion and said effector portion are chemically linked. In specific embodiments, such chemical linkage is a covalent linkage and, in a highly preferred embodiment, such linkage is a peptide bond such that the structurally-stabilized portion and effector portion are part of a single polypeptide chain.

Further in accordance with the invention disclosed herein, the contribution of a chaperone, such as FimC or PapD, to the overall structure of a pilin, such as in the FimC-FimH complex, or in the PapD-PapK complex, was determined by solving the structure of such complexes by X-ray diffraction [see: Choudhury et al, X-ray Structure of the FimC-FimH Chaperone-Adhesin Complex from Uropathogenic *E. coli, Science* 285, 1061 (1999); Sauer et al, Structural Basis of Chaperone Function and Pilus Biogenesis, *Science* 285, 1058 (1999); Barnhart et al., PapD-like Chaperones Provide the Missing Information for Folding of Pilin Proteins, *Proc. Natl. Acad. Sci. USA,* 10, 1073/pnas.130183897 (published online Jun. 20, 2000), the disclosures of all of which references are hereby incorporated by reference in their entirety].

Such donor-strand complemented subunits are referred to herein as "dsc-subunits," for example, as a "dsc-pilin" or "dsc-adhesin" such as "dsc-FimH" or "dsc-PapG." These dsc-subunits have a missing b-strand, for example (see FIG. 1 for domain structure of an adhesin, such as FimH), derived from the N-terminal extension of another subunit, linked to the C-terminus of said subunit, such as by a short amino acid linker. This missing b strand, when replaced by a donor strand sequence, thereby allows the dsc-subunit to fold into a native-like conformation in the absence of the chaperone. The dsc-subunits are thus stable, unlike wild type counterparts present in the periplasm. In accordance with the present invention, such stabilized subunits are linked to effector molecules, such as polypeptides, including antibodies, thereby providing highly useful therapeutic agents.

Thus, in one embodiment of the present invention, a donor strand complementary sequence (or dsc sequence) is used to stabilize a pilus-subunit structure, such as FimH, so as to facilitate the recovery of such structure in a native form useful in formulating vaccines and useful in targeting molecules of therapeutic value to desired locations. In general, the pilus subunits found in bacterial pili have proved difficult to purify in a native immunologically active form. As stated above, this is due mostly to the formation of an immunoglobulin-like fold that must be supplemented by an additional oligopeptide structure. During assembly of pili, this structure is contributed by a periplasmic chaperone, such as FimC or PapD. Once the subunit has been assembled into the pilus the structure is stabilized by an N-terminal sequence of an already inserted pilus protein. Thus, FimH is stabilized by a donor strand provided by FimC during pilus assembly and later stabilized by an N-terminal sequence of FimG once in the pilus.

Such pilus-protein constructs are readily formed by a variety of mechanisms. In one non-limiting example, a pilus protein, such as FimH, which is an adhesin, is co-purified along with a periplasmic chaperone, such as FimC, to form a FimCH complex, thereby stabilizing the otherwise unstable FimH structure. This complex can be dissociated in the presence of urea so as to maintain the dissociated FimH in a stable conformation. To this is then added a desired moiety attached, covalently or otherwise, to a donor strand complementary segment similar to that supplied by the chaperone or by some other pilus subunit, which donor strand complementary segment then insinuates itself into the pilus protein structure thereby simultaneously serving to attach the effector component to the pilus protein and thus forming the pilus-protein construct of the invention. This construct is then separated from the chaperone and urea medium and utilized as a vaccine or other therapeutic entity depending on the function and identity of the effector portion or on the multi-functional activity of the pilus protein construct in the form of a stabilized pilus-protein/effector complex.

Thus, the pilus protein construct of the invention comprise a pilus-protein subunit that is structurally stabilized by a donor strand sequence (to form a dsc-subunit or donor-strand complemented subunit) advantageously provided by an auxiliary structure that makes up a portion of the effector portion of the protein construct. This latter component is commonly a structure that comprises a polypeptide, such as an antibody molecule or some antigenic structure useful in forming a vaccine, but is not limited to such entities. Thus, in an appropriate embodiment, a small organic molecule, such as a therapeutic agent, for example, some type of anti-microbial agent or anticancer agent, can be used. In such an embodiment, the only property this second component should have in order to be useful in the present invention is the ability to provide a dsc sequence for stabilizing the pilus protein portion of the construct and, optionally, the ability to confer a therapeutic effect on the overall construct.

The pilus protein component of the constructs of the invention are commonly component subunit proteins of bacterial surface structures assembled into their respective structure by the aforementioned usher-chaperone pathway. Some thirty or more examples of such bacterial surface structures assembled by the bacterial usher-chaperone pathway are known and include, but are not limited to, systems such as P pilus of *E. coli,* wherein PapD serves as chaperone and PapC as the usher, and which may be involved in such diseases as cystitis and pyelonephritis.

Other diseases that may involve such structures are UTI (urinary tract infections), NBM (newborn meningitis), meningitis, otitis media, Brazilian purpuric fever, whooping cough, gastroenteritis, salmonellosis, astroenteritis, nosocomial UTI, diarrhea, entercolitis, plague and others.

The structures involved in such disease processes are varied and include atypical structures such as F1 antigen of *Yersinia pestis,* the agent of plague, wherein caf1M serves as chaperone and caf1A as usher. The same organism exhibits PH6 antigen with PsaB as chaperone and PsaC as usher.

Other fibers include Type 1 pili, F1C pili, S pili, Hif pili, Haf pili, Types 2 and 3 pili, Pef pili, Lpf pili, MR/P pili, PMF pili, Aft pili, AF/R1 pili, K99 pili, K88 pili, 987P pili, F17 pili, and MR/K (Type 3) pili (the latter found in *Klebsiella pneumoniae,* where MrkB is chaperone and MrkC is usher). Other organisms exhibiting such structures include *Proteus mirabilis, Yersinia enterititis,* as well as forms of enterotoxigenic *Escherichia coli* and rabbit enteropathogenic *E. coli.*

Other types of structures in clude non-fibrial adhesins like the members of the NFA1–6 family, Afa-1, Dr/Afa-111 and M, all found in *E. coli,* as well as atypical structures such as CS3, CS31A pili, CS6 pili, AAF/1, Sef, F1 antigen, PH6 antigen and Myf.

Among the various types of chaperones are also such proteins as PrsD, FocC, AfaE, HifB, HafB, FimB (FhaD), PefD, LpfB, MrpD, PmfD, AftB, AfrC, PaeE, FanE, FasB, F17D, MrkB, NfaE, AfaB, DraE, BmaB, Cs3-1, ClpE, CssC, AggD, SefB, Caf1M, PsaB, PsaB, MyfB and RalE.

Among the different types of ushers known are PapC, PrsC, FimD, FocD, SfaF, HifC, HafC, FimC (FhaA), PefC, LpfC, MrpC, PmfC, AftC, AfrB, FaeD, FanD, FasD, F17papC, MrkC, NfaC, AfaC, DraD, BmaC, Cs3-2, ClpD, CssD, AggC, SefC, Caf1A, PsaC, MyfC and RalD.

Further, in accordance with the foregoing, the conserved chaperone-usher pathway participates in the biogenesis of over thirty multi-subunit organelles, including fiber-like structures termed pili, on the surface of many bacterial species. The pathway name reflects the role of the members of two protein families—the periplasmic chaperones and the outer membrane ushers—in the organelle assembly. Each organelle is assembled by a dedicated chaperone-usher pair. The chaperone binds to each subunit of the organelle in the periplasm, facilitating subunit folding, stabilizing it in a soluble heterodimer complex, and capping a subunit interactive surface. The chaperone thus prevents subunit misfolding, non-productive subunit aggregation, and premature subunit polymerization. The subsequent dissociation of the chaperone from the subunit exposes subunit interaction surfaces that drive their assembly into the organelle. The outer membrane usher forms a pore that allows the passage of the growing organelle through the outer membrane.

The chaperone consists of two domains, each with an immunoglobulin-like (Ig) fold. A typical Ig fold consists of seven strands (strands A–G) that form a two-sheet sandwich around the hydrophobic core of the fold. Each subunit (also termed a pilin in the case of a pilus organelle) also has an Ig fold; however, the subunit fold lacks the canonical seventh strand (strand G), leaving a deep groove on its surface. In a mechanism termed donor strand complementation, the chaperone donates a portion of its G1 strand (the G strand of the N-terminal domain) to complete the Ig fold of the subunit. Each subunit also has an N-terminal extension (normally approximately 6–30 amino acids) that does not contribute to the subunit fold. During organelle assembly, in a process termed donor strand exchange, the N-terminal extension of one subunit occupies the groove of the preceding subunit that was formerly occupied by the G1 strand of the chaperone. Thus, in the mature organelle, each subunit contributes an element to the fold of its neighbor. Such subunit-subunit interactions are very stable. Certain subunits have a receptor-binding domain instead of an N-terminal extension (FIG. 1) and are non-exclusively termed adhesins. For example, the FimH adhesin has a mannose-specific receptor-binding domain, while the PapG adhesin has a receptor-binding domain specific for the globoseries of glycolipids. The lack of a canonical N-terminal extension is consistent with the localization of FimH and PapG at the tips of their respective pili (type1 and P pili), where there is no preceding subunit whose fold needs to be completed.

The missing strand (termed the donor strand) can be provided directly to the subunit to produce a donor-strand-complemented (dsc) subunit. For example, the N-terminal extension of FimG, which completes the fold of FimH in the type 1 pilus, can be fused by a short peptide linker (in this case, four amino acids) to the C-terminus of FimH to produce dscFimH. This dscFimH, unlike wild-type FimH, is stably expressed in the absence of the chaperone. The donor strand can also be linked to the subunit non-covalently.

A portion of the invention described here includes both methods of linking compounds or proteins to pilins via a donor strand as well as the molecules so produced. In a broader sense, the invention includes both methods of using a donor element, be it a strand, helix, or other element, to link compounds or proteins to other proteins, including pilins, that have an element of their folding missing as well as the molecules so produced. FIGS. 1–8 disclosed herein diagram donor strand complementation and exchange, donor-strand-complemented subunits, and several non-exclusive examples of the invention described herein. FIGS. 1–8 are topology diagrams, in which arrows represent strands.

In accordance with the foregoing, specific embodiments of the present invention relate to an isolated protein construct as described herein wherein said pilus-protein is a protein that in living bacterial cells acts as a substrate for assembly into a bacterial surface structure by the usher-chaperone pathway.

In separate embodiments, the present invention relates to isolated protein constructs wherein said pilus-protein is a pilin, especially a pilin selected from the group consisting of FimH, FimA, FimG, FimF, PapG, PapA, PapE, PapF, and PapK and to isolated protein constructs wherein said pilus-protein is an adhesin, especially an adhesin selected from the group consisting of FimH and PapG.

The present invention also includes isolated protein constructs as disclosed herein wherein the pilus-protein portion is an active fragment of a pilus-protein, including N-terminal deleted pilus proteins. Active fragments of any or the pilus-proteins disclosed herein are potentially useful in practicing the claimed invention, such as active fragments of pilins and adhesins.

In accordance with the present invention the pilus-subunit N-terminal extensions participate in subunit-subunit interactions in the mature organelle but does not contribute to the fold of the of the subunit and thus can be eliminated so as to produce a stable subunit not capable of undergoing the aforementioned donor strand exchange reaction with other subunits or with chaperone-subunit complexes. As demonstrated herein, N-terminal deleted PapE (Ntd-PapE), wherein residues 2–12 (representing most of the N-terminal extension) have been eliminated through genetic engineering, has been expressed and purified in complex with PapD. Complexes of PapD with wild type PapE undergo polymerization reactions to yield complexes with PapE-PapE interactions whereas complexes of PapD with Ntd-PapE do not undergo such interactions.

The present invention also relates to methods of forming the protein constructs of the invention. Commonly, the pilus-protein portion and the effector portion of the protein constructs of the invention are linked using a donor strand, such as a donor strand complementing sequence. In specific embodiments of the present invention said donor strand is covalently linked to at least one of said pilus-protein portion or said effector portion, especially where said donor strand is covalently linked to said pilus-protein portion but not to said effector portion or where said donor strand is covalently linked to said effector portion but not to said pilus-protein portion. In a highly specific embodiment, said donor strand is covalently linked to both said pilus-protein portion and said effector portion. In another highly specific embodiment, said donor strand is non-covalently linked to said pilus-protein portion and to said effector portion.

Also in accordance with the foregoing, the isolated protein constructs, especially isolated protein constructs, of the present invention are protein constructs wherein said pilus-protein is a protein that in living bacterial cells acts as a substrate for assembly into a bacterial surface structure by the usher-chaperone pathway.

In specific embodiments, the present invention relates to protein constructs, especially isolated protein constructs, wherein said pilus-protein is a pilin, especially a pilin selected from the group consisting of FimH, FimA, FimG, FimF, PapG, PapA, PapE, PapF, and PapK.

In specific embodiments, the present invention also relates to protein constructs, especially isolated protein constructs, wherein said pilus-protein is an adhesin, especially an adhesin selected from the group consisting of FimH and PapG.

In other specific embodiments, such protein constructs include protein constructs wherein said pilus-protein portion is an active fragment of a pilus-protein.

The present invention also relates to antibodies specific for the protein constructs of the invention, which protein constructs, isolated or not, are useful as vaccines for eliciting an immunogenic response.

The present invention also relates to a process for preparing the protein constructs disclosed according to the invention comprising linking a pilus protein moiety, or active fragment moiety thereof, to an effector moiety via a bridging structure comprising a donor strand.

In specific embodiments, the process according to the present invention includes use of a donor strand that is covalently linked to said pilus-protein or to said active portion of said pilus-protein, including processes wherein said donor strand is covalently linked to said effector moiety and non-covalently linked to said pilus protein moiety or active fragment moiety thereof. In a specific embodiment, the present invention relates to a process wherein said pilus-protein moiety, or active fragment moiety, is an N-terminal deleted pilus-protein moiety or active fragment moiety.

In the broadest sense, the present invention relates to a protein construct comprising a pilus-protein portion linked to an effector portion. In specific embodiments, said effector portion may be an immunoglobulin, an adjuvant or some other protein or polypeptide, including another pilus-protein, thus forming a pilus protein dimer, tetramer or other multimeric structure with multiple antigenic sites.

As used herein, the term "effector portion" refers to a portion of the protein constructs of the invention other than a pilus-protein portion, or fragment thereof, and wherein said effector portion confers on the protein construct a discernible physiological property other than that realized by the pilus-protein subunit, or fragment thereof, alone, including any kind of immunological effect, such as where vaccine activity is conferred that is in addition to any such activity produced by the pilus protein alone. Such effector may include such structures as a polypeptide or polynucleotide, an adjuvant, an immunoglobulin, which is a polypeptide, another pilus protein subunit or any of a variety of small molecules, such as an oligopeptide, an oligonucleotide, or small organic molecules with antimicrobial, antibacterial or other physiological and/or therapeutic or prophylactic effects in an animal, such as a human. Where such effector is another pilus protein, the result is a dimer or trimer or higher order multimeric structure and the physiological effect realized is greater than that of a single pilus protein subunit by itself.

Figure 7:
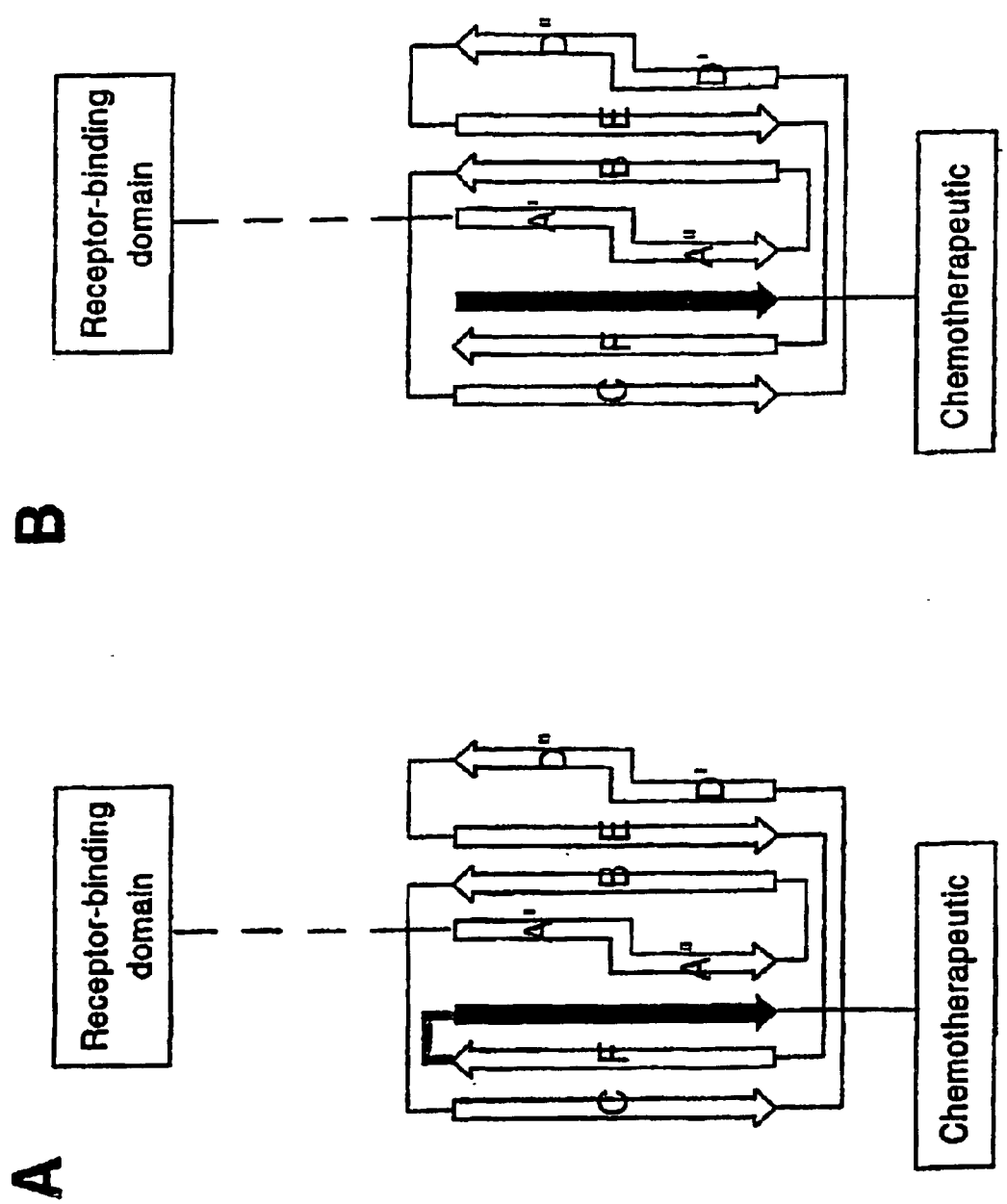
FIG. 7. Examples of the invention—chemotherapeutic linked to an adhesin via a donor strand. The chemotherapeutic is represented as a labeled box joined to the donor strand. A. Covalent linkage of the donor strand. B. Non-covalent linkage of the donor strand. Such adhesin-chemotherapeutic molecules are potentially useful as tissue-specific anti-cancer therapeutics, since the various adhesins are tissue specific.
Figure 8:
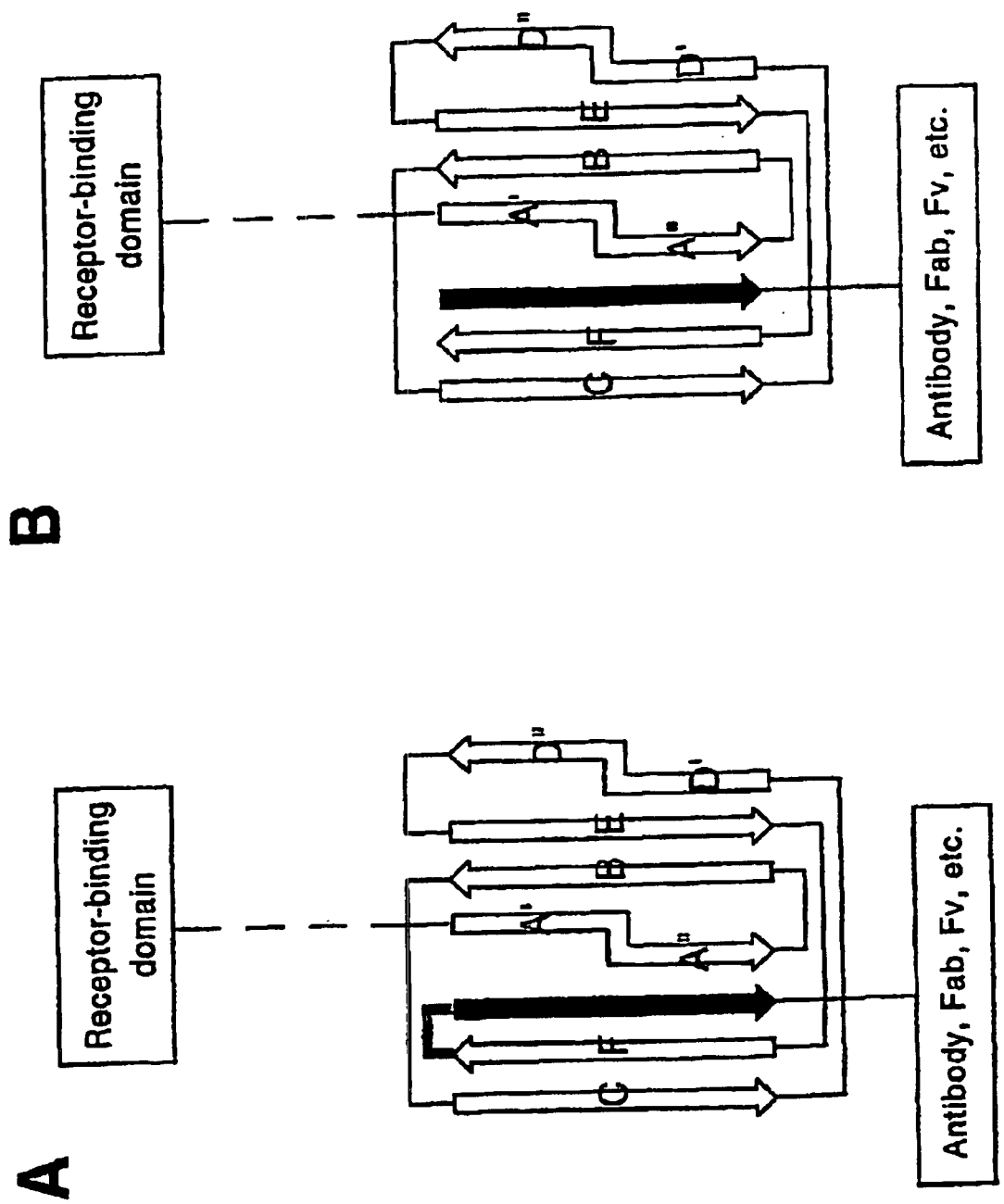
FIG. 8. Examples of the invention—antibody or antibody fragment linked to an adhesin via a donor strand. The antibody or antibody fragment is represented as a labeled box joined to the donor strand. A. Covalent linkage of the donor strand. B. Non-covalent linkage of the donor strand. Such adhesin-antibody molecules are potentially useful as tissue-specific anti-cancer, anti-bacterial, or anti-viral agents.

In one embodiment of the present invention, the effector portion comprises a chemotherapeutic agent, as shown in FIG. 7, wherein said agent is an antimicrobial or anticancer agent. Such agent may also be a cytoprotective agent.

In another embodiment of the present invention, the effector portion of the protein construct comprises an antibiotic, especially a polypeptide antibiotic, most especially wherein a portion of said polypeptide antibiotic comprises a donor strand, attached thereto either covalently or non-covalently, thereby serving to link said effector portion to said pilus-protein portion to form a protein construct.

In one embodiment of the present invention, a pilus protein construct incorporates as an effector portion an immunoglobulin that has linked thereto a donor strand segment serving to attach the immunoglobulin to, and stabilize, the pilus protein portion of the construct.

As used herein, the term "immunoglobulin" is not limited to the traditional definition of an antibody but can include molecules merely having antibody-like structures, functions and specificities. With the advent of methods of molecular biology and recombinant technology, it is now possible to produce immunoglobulin molecules by recombinant means and thereby generate gene sequences that code for specific amino acid sequences found in the polypeptide structure of the immunoglobulin. Such molecules, for use as the effector portion of the structures of the present invention, can be produced by either cloning the gene sequences encoding the polypeptide chains of said antibodies or by direct synthesis of said polypeptide chains, with in vitro assembly of the synthesized chains to form active tetrameric ($H_2L_2$) structures with affinity for specific epitopes and antigenic determinants, for example, those found on bacteria and viruses and other microorganisms. This has permitted the ready production of antibodies having sequences characteristic of neutralizing antibodies from different species and sources.

Regardless of the source of the immunoglobulins, or how they are recombinantly constructed, or how they are synthesized, in vitro or in vivo, using transgenic animals, such as cows, goats and sheep, using large cell cultures of laboratory or commercial size, in bioreactors or by direct chemical synthesis employing no living organisms at any stage of the process, all immunoglobulins, including antibodies, have a similar kind of overall 3 dimensional structure. For a conventional antibody, this structure is often given as $H_2L_2$ and refers to the fact that antibodies commonly comprise 2 light (L) amino acid chains and 2 heavy (H) amino acid chains. Both chains have regions capable of interacting with a structurally complementary antigenic target. The regions interacting with the target are referred to as "variable" or "V" regions and are characterized by differences in amino acid sequence from antibodies of different antigenic specificity.

The variable regions of either H or L chains contains the amino acid sequences capable of specifically binding to antigenic targets. Within these sequences are smaller sequences dubbed "hypervariable" because of their extreme variability between antibodies of differing specificity. Such hypervariable regions are also referred to as "complementarity determining regions" or "CDR" regions. These CDR regions account for the basic specificity of the antibody for a particular antigenic determinant structure.

The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all antibodies each have 3 CDR regions, each non-contiguous with the others (termed L1, L2, L3, H1, H2, H3) for the respective light (L) and heavy (H) chains. The accepted CDR regions have been described by Kabat et al, *J. Biol. Chem.* 252:6609–6616 (1977).

In all mammalian species, antibody polypeptides contain constant (i.e., highly conserved) and variable regions, and, within the latter, there are the CDRs and the so-called "framework regions" made up of amino acid sequences within the variable region of the heavy or light chain but outside the CDRs.

Thus, in accordance with the present invention, the immunoglobulin forming the auxiliary structure or portion of the pilus-protein constructs of the present invention may be composed of tetrameric antibody structures, or dimeric structures comprising a heavy and light chain, or of just heavy or light chains, or of substructures of these, such as one or more CDR regions linked together, with or without specific amino acids being incorporated at selected locations in either the CDR or framework regions, or both, or of specific kinds of fragments of these structures, such as Fab or $F(ab)'_2$ fragments, methods for forming which being well known in the art.

In preferred embodiments, the auxiliary component is selected from the group consisting of a tetrameric antibody, a dimeric antibody, especially a dimer composed of at least one heavy chain and at least one light chain of an antibody, a chimeric antibody, formed from polypeptide chains selected from different species or other sources, a recombinant antibody, an immunogenic fragment of an antibody.

Thus, in accordance with the present invention, the immunoglobulin forming the effector portion of the protein constructs of the present invention may be composed of tetrameric antibody structures, or dimeric structures comprising a heavy and light chain, or of just heavy or light chains, or of substructures of these, such as one or more CDR regions linked together, with or without apecific amino acids being incorporated at selected locations in either the CDR or framework regions, or both, or of specific kinds of fragments of these structures, such as Fab or $F(ab')_2$ fragments, methods for forming which being well known in the art.

In preferred embodiments, the effector portion is selected from the group consisting of a tetrameric antibody, a dimeric antibody, especially a dimer composed of at least one heavy chain and at least one light chain of an antibody, a chimeric antibody, formed from polypeptide chains selected from different species or other sources, a recombinant antibody, an immunogenic fragment of an antibody.

In one non-limiting example, a donor strand complementary segment is linked by its C-terminus to the C-terminus of at least one strand of a heavy chain of an antibody whereupon, after being combined with the pilus protein, such as in the urea-containing medium mentioned above, or other suitable stabilizing medium, said donor strand complementary segment binds to and stabilizes the structure of the pilus protein and thereby forms a pilus protein construct comprising the structurally (dsc) stabilized pilus protein linked to the antibody molecule. Because and antibody commonly has two heavy chains it can advantageously be linked to two donor strand complementary sequences and thereby provide a divalent dsc-stabilizing structure available for attaching to and stabilizing two pilus protein structures of like or different identity, thus providing a truly multivalent structure. Of course, the dsc-segment can be linked to the antibody at any convenient points in its structure but the C-terminal end of the heavy chain, or chains, provides a site physically removed from the antigenic binding sites present near the N-terminal ends of the heavy and light chain variable regions required to confer antigenic specificity on the antibody. In addition, in forming such multivalent structures, the dsc-segments also need not be identical but may differ in their sequences. For example, one such structure may comprise the dsc-strand derived from a periplasmic chaperone, such as FimC or PapD, attached to one C-terminus of the antibody while the other dsc-strand is derived from the N-terminal region of a pilus subunit, such as FimG, which can also serve to stabilize otherwise unstable pilus subunits.

In preferred embodiments, such antibody structures as just mentioned will commonly have neutralizing ability and will exhibit specificity for antigenic determinants present on bacterial cells, especially enterobacilli such as *E. coli,* most especially where said antibody, or antibody structure, has specificity for at least one antigenic site or determinant found of *E. coli.*

In accordance with the foregoing, a pilus-protein construct of the invention has an auxiliary component comprising an immunoglobulin wherein the latter may include at least one heavy and one light chain of an antibody or may include an entirely functional tetrameric structure comprising two light and two heavy chains in the classic antibody arrangement or simply a functional fragment of such antibody (e.g., an Fab or F(ab)'$_2$ structure). In preferred embodiments of this structure the antibody has specificity for at least one antigenic determinant of a microorganism, especially wherein said microorganism is selected from the group consisting of viruses, bacteria, fungi and protozoans, preferably wherein said microorganism is a bacterium, most especially *Escherichia coli.*

Thus, antibodies useful in practicing the present invention may have specificity for antigenic determinants found on microbes and are capable of neutralizing said microbes by attaching thereto. In accordance with the present invention, such microbes are most often viruses, bacteria or fungi, especially organisms that cause respiratory disease and most preferably viruses. A specific example, used in the examples herein, is respiratory syncytial virus (RSV); another example is parainfluenza virus (PIV).

In a specific embodiment, a neutralizing antibody useful in practicing the present invention includes such available antibodies as MEDI-493, which is an $Ig_1$ (COR)/kappa (K102) humanized MAb (heavy and light chain variable region sequences shown in U.S. Pat. No. 5,824,307, FIGS. 7 and 8 therein) containing the antigen binding determinants of murine MAb 1129 [Johnson et al, *J. Infect. Dis.,* 176, 1215–1224 (1997); Beeler and van Wyck Coelingh,*J. Virol.,* 63, 2941–2950 (1989)].

In one embodiment, the antibodies comprising the effector portion of the protein constructs of the invention are high potency neutralizing or non-neutralizing antibodies. Such high potency antibodies may, for example, have specificity for antigens displayed on the surfaces of cancer cells and may include antibodies, such as VITAXIN®, that are non-neutralizing. (See: Wu et al., *Proc. Natl. Acad. Sci.* 95:6037–6042 (1998)) The antibodies of the present invention also include antibodies for use in other non-neutralizing reactions.

In a specific but non-limiting example of such embodiment, the dsc-stabilized pilus protein is FimH, which is known to have a mannose-binding region near the N-terminus of the single polypeptide chain making up this adhesin. Of course, the dsc-segment need not be provided by the auxiliary structure but may be engineered into the pilus protein structure, for example, by linking it covalently, such as via a peptide bond, to the C-terminus of said pilus protein. Thus, FimH has been structurally stabilized by actually engineering a dsc-sequence at the C-terminal end of its polypeptide chain (see U.S. patent application Ser. No. 09/615,846, filed Jul. 13, 2000, the disclosure of which is hereby incorporated by reference in its entirety. Of course, as described above, a dsc-sequence can be provided by the auxiliary structure forming part of the pilus protein construct of the invention. Thus, attachment of the dsc-sequence to the C-terminus of an antibody, or active fragment of an antibody, said location being opposite the antigen binding domains of the antibody (located at the N-terminal ends thereof) makes the dsc-sequence available for binding to FimH, thereby stabilizing the latter in its native conformation. The resulting pilus-protein construct, here a structurally stabilized FimH construct, is thereby able to use its mannose-binding domain to target the construct to the bladder where the antibody, having, for example, antibacterial activity, is able to combat bacterial infections of the bladder, such as urinary tract infections caused by *E. coli.*

In another such embodiment, the pilus-protein construct comprises as a portion thereof an adjuvant, or that is capable of acting as an adjuvant under appropriate conditions, and wherein immunological activity, such as vaccine-like activity, is provided by the donor-strand stabilized pilus protein portion of the construct. For example, adhesins such as FimH, once they have been structurally stabilized by the presence of a dsc-sequence, optionally attached to and provided by the adjuvant, are useful as vaccines. Utility as a vaccine is thereby greatly increased by the presence of said adjuvant linked to the stabilized pilus-protein. In one embodiment, the structurally stabilized pilus protein is FimH stabilized by a dsc-sequence contributed by a dsc-strand attached to an adjuvant or where the dsc-strand has been genetically engineered to form the C-terminal end of the FimH polypeptide sequence and said adjuvant is linked, covalently or otherwise, to the dsc-FimH structure to form a FimH construct exhibiting both structural stability and potent immunogenic activity. Here the dsc-stabilized FimH portion of the construct serves to target the adhesin-adjuvant complex to a desired target area, such as tissues exhibiting mannosyl-sites for binding to the mannosyl binding domain of the FimH, which is mostly in the N-terminal two thirds of the molecule, with the attendant adjuvant available for an immunogenic boost to the resultant antibody generating, or other immunological, activity.

Immunostimulatory adjuvants useful in practicing the present invention include, but are not limited to, cytokines (e.g., interleukin-2, interleukin-7, interleukin-12, granulocyte-macrophage colony stimulating factor (GM-CSF), interferon-gamma, interleukin-2 (IL-2), and IL-1 peptide or Sclavo Peptide, cytokine-containing liposomes, triterpenoid glycosides or saponins (e.g., QuilA and QS-21, also sold under the trademark STIMULON™, ISCOPREP™), Muramyl Dipeptide (MDP) derivatives, such as N-acetyl-muramyl-L-threonyl-D-isoglutamine (Threonyl-MDP, sold under the trademark TERMURTIDE™), GMDP, N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine, muramyl tripeptide phosphatidylethanolamine (MTP-PE), unmethylated CpG dinucleotides and oligonucleotides, such as bacterial DNA and fragments thereof, LPS, monophosphoryl Lipid A (3D-MLA sold under the trademark MPL), and polyphosphazenes.

In another embodiment, the adjuvant used is a CpG adjuvant. Oligodeoxynucleotides (ODN) containing unmethylated CpG dinucleotides within specific sequence contexts (CpG motifs) are detected, like bacterial or viral DNA, as a danger signal by the vertebrate immune system. CpG ODN synthesized with a nuclease-resistant phosphorothioate backbone have been shown to be a potent Th1-directed adjuvant in mice. In addition, an ODN with a TpC dinucleotide at the 5' end followed by three 6 mer CpG motifs (5'-GTCGTT-3') separated by TpT dinucleotides has shown high immunostimulatory activity for human, chimpanzee, and rhesus monkey leukocytes (Hartmann et al., J. Immun, 164: 1617–1624 (2000)).

In another embodiment, suitable adjuvants include, but are not limited to: N-acetyl-muramyl-L-threonyl-D-isoglutamine (thr-MDP), Bacetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine. In another embodiment, the adjuvant used is a particulate adjuvant, including, but not limited to, emulsions, e.g., squalene or squalane oil-in-water aduvant formulations, such as SAF, e.g., prepared with block-copolymers, such as L-121 (polyoxypropylene/polyoxyethylene) sold under the trademark PLURONIC™ L-121, Liposomes, Virosomes, cochleates, and imune stimulating complex, which is sold under the trademark ISCOM™. Freund's Complete Adjuvant and Freund's Incomplete Adjuvant are also commonly used adjuvants in test animals, however these adjuvants are less preferred in primates, in particular for use in humans.

In another embodiment, a microparticulate adjuvant is used. Microparticulate adjuvants include, but are not limited to biodegradable and biocompatible polyesters, homo- and copolymers of lactic acid (PLA) and glycolic acid (PGA), poly(lactide-co-glycolides) (PLGA) microparticles, polymers that self-associate into particulates (poloxamer particles), soluble polymers (polyphosphazenes), and virus-like particles (VLPs) such as recombinant protein particulates, e.g., hepatiis B surface antigen (HbsAg).

Yet another class of adjuvants that may be used include mucosal adjuvants, including but not limited to heat-labile enterotoxin from *Escherichia coli* (LT), cholera holotoxin (CT) and cholera Toxin B Subunit (CTB) from *Vibrio cholerae,* mutant toxins (e.g. LTK63 and LTR72), microparticles, and polymerized liposomes. Additional examples of mucous targeting adjuvants are *E. coli* mutant heat-labile toxin LT=s with reduced toxicity, live attenuated organisms that bind M cells of the gastrointestinal tract, such as *V. cholera* and *Salmonella typhi, Mycobacterium bovis* (BCG), in addition to mucosal targeted particulate carriers such as phospholipid artificial membrane vesicles, copolymer microspheres, lipophilic immune-stimulating complexes and bacterial outer membrane protein preparations (proteosomes).

In other embodiments, any of the above classes of adjuvants may be used in combination with each other or with other adjuvants. For example, non-limiting examples of combination adjuvant preparations that can be used to administer the compositions of the invention include liposomes containing immunostimulatory protein, cytokines, or T-cell and/or B-cell peptides, or microbes with or without entrapped IL-2 or microparticles containing enterotoxin. Other adjuvants known in the art are also included within the scope of the invention (Vaccine Design: The Subunit and Adjuvant Approach, Chap. 7, Michael F. Powell and Mark J. Newman (eds.), Plenum Press, New York, 1995, which is incorporated herein in its entirety).

The effectiveness of an adjuvant may be determined by measuring the induction of specific antibodies directed against a composition formulated with the particular adjuvant.

In a specific embodiment, a pilus protein construct comprises a structurally stabilized HifE protein of *Haemophilus influenzae* linked to an adjuvant to form a HifE vaccine. Such a vaccine is useful in preventing such diseases as otitis media.

The present invention also relates to compositions comprising the pilus-protein constructs of the invention suspended in a pharmacologically acceptable carrier. The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids such as water, saline, glycerol and ethanol, and the like, including carriers useful in forming sprays for nasal and other respiratory tract delivery or for delivery to the ophthalmic system. A thorough discussion of pharmaceutically acceptable carriers, diluents, and other excipients is presented in REMINGTON'S PHARMACEUTICAL SCIENCES (Mack Pub. Co., N.J. current edition).

Such compositions are useful inter alia as vaccines. Thus, the present invention also relates to a vaccine comprising a prophylactically effective amount of a pilus-protein construct of the invention suspended in a pharmacologically acceptable carrier as described. In accordance with the foregoing, the present invention also relates to a process for preventing a disease in a human patient comprising administering to a patient at risk of said disease of a prophylactically effective amount of a vaccine of the invention. In a preferred embodiment, said disease is a urinary tract infection, especially a urinary tract infection is caused by a bacterium, most especially wherein said bacterium is *Escherichia coli.*

Because the pilus-protein constructs of the invention can comprise an antibody or other therapeutically active moiety, the present invention also relates to a process for treating a disease in a human patient comprising administering to a patient afflicted with said disease of a therapeutically effective amount of a pilus-protein construct of the invention wherein said construct comprises a therapeutically effective moiety, such as an antibody. In a preferred embodiment, said disease is a urinary tract infection, especially a urinary tract infection is caused by a bacterium, most especially wherein said bacterium is *Escherichia coli* and said antibody is effective in reducing bacterial titer.

Further in accordance with the present invention, the pilus-protein construct of the invention comprises any pilus protein used in nature for assembly into a pilus via the usher-chaperone pathway described above. In preferred but non-limiting embodiments the present invention relates to a pilus-protein construct wherein said dsc-stabilized pilus protein is a dsc-stabilized pilin, most preferably a pilin selected from the group consisting of FimH, FimA, FimG, FimF, PapG, PapA, PapE, PapF, and PapK, especially wherein said dscstabilized pilus protein is an adhesin, most especially FimH or PapG.

In an additional embodiment, a pilus-protein construct of the invention may comprise an oligonucleotide or polynucleotide sequence, wherein said oligonucleotide or polynucleotide sequence is chemically linked, either covalently or non-covalently, to a dsc-segment that serves both to stabilize the pilus-protein portion of the construct and to associate the oligonucleotide or polynucleotide with the dsc-stabilized pilus protein portion, thereby affording a pilus protein construct that is a physiologically stable protein-polynucleotide complex.

It should be noted that the invention disclosed herein is not limited to the use of dsc-subunits as the pilus-protein portion but includes non-dsc-subunits, including any subunit or portion thereof, that is linked, by either genetic or chemical means, or by other means known to those skilled in the art, to an additional moiety, such as an antibody or adjuvant, with therapeutic activity. In forming such structures, the portions thereof may be linked covalently or not. In one such embodiment, co-expression of, or in vitro combination of wild type FimH with an antibody and having a donor strand genetically engineered at either its N- or C-terminus would yield a FimH molecule whose immunoglobulin, or Ig, fold is completed by the donor strand attached to the antibody and thus is non-covalently linked to the antibody.

In forming the structurally-stabilized portions of the protein constructs of the invention, structural stabilization can be achieved in different ways. A preferred embodiment of the present invention employs the use of a donor strand complementation mechanism for stabilization of pilus-proteins found in bacterial species, especially E. coli. Thus, in a preferred embodiment, the structurally stabilized pilus protein portion is a donor strand complemented pilus-protein, especially an adhesin. Such adhesins are commonly selected from the group consisting of FimH and PapG. In general, pilus-proteins useful in forming the structurally-stabilized portion of the proteins, or structures, of the present invention are selected from the group consisting of FimH, FimA, FimG, FimF, PapG, PapA, PapE, PapF, and PapK.

As used herein, the term "donor strand complementation" or "donor strand complemented" refers to a protein, especially a pilus-protein, including pilins or adhesins, most especially a pilus-protein found in E. coli cells, whose structure has been stabilized by attachment, especially through formation of a peptide bond, of a sequence of amino acids found in a bacterial chaperone, commonly a chaperone derived from the same species as the pilus-protein, although not necessarily the same strain of that species. Such chaperone-derived sequence is commonly attached to the C-terminal end of the amino acid sequence of the pilus-protein and serves to maintain the native conformation of said pilus-protein. Such a means of stabilization has been described in U.S. provisional patent application Nos. 60/144359, filed Jul. 16, 1999, and 60/184442, filed Feb. 23, 2000, and U.S. application Ser. No. 09/615,846, filed Jul. 13, 2000, the disclosures of which are hereby incorporated by reference in their entirety.

It is contemplated that the protein constructs of the present invention may be in isolated or purified form. Since such structures have not been found in nature, it is contemplated that, after formation by methods as disclosed herein, said constructs can be isolated and purified by means well known to those skilled in the art of protein purification and detailed means of isolated and purification need not be further described. The protein constructs of the present invention need be isolated and purified only to the extent required for their intended purpose. Thus, a high degree of purification may not be in order where the purpose is to generate a monoclonal antibody specific for one or more antigenic determinants present on said construct.

"Isolated" in the context of the present invention with respect to protein constructs means that the material is removed from its original environment (e.g., the cells used to recombinantly produce the polypeptides disclosed herein). Such peptides could be part of a composition, and still be isolated in that such vector or composition is not part of its natural environment. The polypeptides and polynucleotides of the present invention are preferably provided in an isolated form, and preferably are purified to homogeneity.

The protein constructs disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, polypeptides from individual clones isolated from a cDNA library have been conventionally purified to electrophoretic homogeneity. Purification of starting material or natural material to at least one order of magnitude, preferably two or three orders, and more preferably four or five orders of magnitude is expressly contemplated.

In accordance with the present invention, the term "nucleotide sequence" refers to a heteropolymer of deoxyribonucleotides. Generally, DNA segments encoding the proteins provided by this invention are assembled from cDNA fragments and short oligonucleotide linkers, or from a series of oligonucleotides, to provide a synthetic gene which is capable of being expressed in a recombinant transcriptional unit comprising regulatory elements derived from a microbial or viral operon.

As used herein, reference to a DNA sequence, including an oligonucleotide or polynucleotide, includes both single stranded and double stranded DNA. Thus, the specific sequence, unless the context indicates otherwise, refers to the single strand DNA of such sequence, the duplex of such sequence with its complement (double stranded DNA) and the complement of such sequence.

The present invention is also directed to antibodies specific for, and antisera generated in response to, immunogenic protein constructs of the invention. Such antibodies may be either polyclonal or monoclonal and may be generated by methods well known in the art. In addition, the present invention also relates to cells, and cell lines, genetically engineered to produce such antibodies after being transfected, or otherwise transformed, so that their genomes contain, within the main chromosome or as part of a plasmid or other vector, a polynucleotide encoding the genes for an antibody specific for a single polypeptide protein construct of the invention, especially where said engineered cell is a cell capable of forming and secreting a fully formed antibody, such technology being known in the art.

In another aspect of the invention, immunogenic compositions of the invention may be utilized to produce antibodies to diagnose urinary tract infections, or to produce vaccines for prophylaxis and/or treatment of such infections as well as booster vaccines to maintain a high titer of antibodies against the immunogen(s) of the immunogenic composition.

While other antigens have been utilized to produce antibodies for diagnosis and for the prophylaxis and/or treatment of bacterial urinary tract infections, there is a need for improved or more efficient vaccines. Such vaccines should have an improved or enhanced effect in preventing bacterial infections mediated by pilus proteins.

In one aspect, the present invention is directed to an immunogenic composition comprising a purified pilus-protein construct comprising a dsc-pilus protein polypeptide or immunogenic complex thereof attached to an effector portion that confers additional immunogenicity on said protein construct. A specific but non-limiting embodiment comprises a native or modified pilus protein, such as an adhesin, preferably FimH, and a donor strand, such as one derived from a periplasmic chaperone, preferably FimC or PapD, most preferably the G1 strand of FimC, or an amino terminal extension of a pilin, preferably FimG, most preferably no more than the first 17 N-terminal residues of FimG, especially the first 13 residues thereof, with the dsc-pilus-protein maintained in the complex in a structurally stabilized form capable of binding to a region of tissue, such as in the urinary tract, and thereby acting as a targeting vector for conveying a molecule with therapeutic activity, such as a neutralizing antibody, to said region or tissue. Thus, the structurally-stabilized pilus-portion itself will be in immunogenic form capable of inducing an immune response when appropriately introduced into a human or other mammalian species.

Generally, vaccines are prepared as injectables, in the form of aqueous solutions or suspensions. Pharmaceutical carriers are generally added that are compatible with the active ingredients and acceptable for pharmaceutical use. Examples of such carriers include, but are not limited to, water, saline solutions, dextrose, or glycerol. Combinations of carriers may also be used.

Vaccine compositions may further incorporate additional substances to stabilize pH, or to function as adjuvants, wetting agents, or emulsifying agents, which can serve to improve the effectiveness of the vaccine.

Vaccines are generally formulated for parenteral administration and are injected either subcutaneously or intramuscularly. Such vaccines can also be formulated as suppositories or for oral administration, using methods known in the art.

In addition to use as vaccines, the polypeptides of the present invention, and immunogenic fragments thereof, can be used as immunogens to stimulate the production of antibodies for use in passive immunotherapy, for use as diagnostic reagents, and for use as reagents in other processes such as affinity chromatography.

In addition to producing a genetically engineered or synthetic sequence for the complete adhesin-donor strand polypeptide, it is also possible to attach the appropriate donor strand fragment at or near the COOH-end of the adhesin chain by some chemical linker other than a conventional oligopeptide using a standard peptide bond. Such chemically fused structures are contemplated by the present invention, the nature of such structures being limited only by the imagination of chemists seeking to produce functional polypeptides of the invention. Such linking structures also include standard polymers forming an appropriate looping structure or may be by any of the non-covalent interactions listed above. Methods of doing so are suggested in U.S. provisional patent application Nos. 60/144359, filed Jul. 16, 1999, and 60/184442, filed Feb. 23, 2000, and U.S. application Ser. No. 09/615,846, filed Jul. 13, 2000, the disclosures of which are hereby incorporated by reference in their entirety.

Antibodies generated against immunogenic pilus-protein constructs of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides.

In one embodiment, the pilus-protein portion and effector portion may be part of a single polypeptide chain that may itself be encoded by a polynucleotide so that the entire protein construct can be formed by expression of said polynucleotide.

The present invention further relates to a process for treating an infection comprising administering to a patient so infected a therapeutically effective amount of a composition comprising one or more protein constructs of the invention, especially where said infection is a bacterial infection, most especially where said bacterial infection is an infection by *Escherichia coli*.

The present invention further relates to a protein construct, or structure, comprising a structurally stabilized pilus protein portion and an effector portion wherein said effector portion comprises at least one additional, possibly different, pilus protein portion, and wherein the latter may or may not be itself structurally stabilized independent of the structurally-stabilized portion or where said effector portion is structurally-stabilized by its association with said structurally-stabilized portion. In specific embodiments, said structurally stabilized pilus protein portion and said at least one additional pilus-protein portion are chemically linked, especially where said linkage is via a covalent bond, most especially a peptide bond. In a preferred embodiment, said structurally-stabilized portion and said at least one additional pilus-protein portion are part of the same polypeptide chain. Where said additional pilus-protein portion is independently structurally-stabilized, this is preferably accomplished through donor strand complementation according to the present disclosure. In a specific embodiment, such additional pilus-protein portion, including where said portion is stabilized by donor strand complementation, is a pilin selected from the group consisting of FimH, FimA, FimG, FimF, PapG, PapA, PapE, PapF, and PapK, most especially where said additional pilus-protein portion is an adhesin selected from the group FimH and PapG.

In a preferred embodiment, the pilus-protein portion, for example, a dsc-adhesin, especially dsc-FimH or dsc-PapG, is linked to another adhesin, either the same or different from the dsc-adhesin, to form an adhesin dimer (or trimer, or higher order structures) which find use as multivalent vaccines.

In accordance with the foregoing, the present invention further relates to a protein construct, especially an isolated protein construct comprising a pilus protein portion linked to an effector portion wherein said pilus protein portion comprises a single pilus protein, including active fragments thereof, wherein said pilus protein portion is not attached to a bacterial cell and wherein said effector portion comprises a pilus-protein, including active fragments thereof, and wherein said protein construct does not comprise a pilus.

In specific embodiments, the present invention relates to a protein construct, especially an isolated protein construct as disclosed herein wherein said pilus protein and said effector portions each comprises a pilus protein and said pilus-protein is a protein that in living bacterial cells acts as a substrate for assembly into a bacterial surface structure by the usher-chaperone pathway. Said pilus protein may likewise comprises a pilin, especially one selected from the group consisting of FimH, FimA, FimG, FimF, PapG, PapA, PapE, PapF, and PapK, or an adhesin, especially an adhesin selected from the group consisting of FimH and PapG. In such embodiments, the pilus-protein portion may also include an active fragment of a pilus-protein, especially an N-terminal deleted pilus-protein.

In specific embodiments, the present invention relates to a protein construct, especially an isolated protein construct, wherein said pilus-protein portion comprises FimH and said effector portion comprises a complex of FimG and FimC (to form FimCGH). In an additional and separate embodiment, said pilus-protein portion comprises PapE and said effector portion comprises a complex of PapK and PapD, especially wherein said PapE is N-terminal deleted PapE. In the latter embodiment, formation of fibers is potentially possible where the PapE contains it usual N-terminal domain. However, formation of such structure using an N-terminal deleted PapE results in a trimeric structure (PapD-PapK-PapE or PapDKE) that does not form fibers and thus remains available for use as a trimeric immunogenic structure, such as a vaccine, and advantageously presents multiple immunogenic sites for immunological recognition.

In a highly specific embodiment, the present invention relates to a protein construct, especially an isolated protein construct, wherein the pilus protein portion and the effector portion are part of a single polypeptide chain that may or may not contain as part of said polypeptide chain a donor strand amino acid sequence. Where said donor strand amino acid sequence is part of said polypeptide chain, said donor strand complementary sequence will be incorporated into said single chain polypeptide such that the N-terminal portion of said donor strand is linked in a peptide bond to the C-terminal portion of the pilus-protein portion of said protein construct and the C-terminal portion of said donor strand amino acid sequence is linked by a peptide bond to the N-terminal portion of the effector portion. In a separate embodiment, the C-terminal portion of the donor strand amino acid sequence may be linked to the C-terminal portion of the effector portion of the protein construct. Of course, in the latter case a covalent bond different from the conventional peptide bond will be formed between the respective C-termini of the donor strand and the effector portions of the protein construct.

The present invention also relates to a protein construct comprising more than one pilus-proteins or active fragments thereof, such as where the effector portion itself comprises a pilus protein, or active fragment thereof, such that the pilus-protein and effector portions are linked by a donor strand complementary sequence (a sequence that serves to stabilize the pilus-protein portion of the protein construct).

The present invention also relates to a composition comprising a therapeutically, including a prophylactically, effective amount of the protein constructs disclosed herein and suspended in a pharmacologically acceptable carrier, such carrier including all pharmaceutically acceptable diluents and excipients.

Thus, the present invention further relates to a process for treating or preventing a disease comprising administering to a patient afflicted therewith or at risk thereof a therapeutically effective amount of a composition as just described. In preferred embodiments, said disease is a urinary tract infection, especially wherein said urinary tract infection is caused by a bacterium, most especially wherein said bacterium is *Escherichia coli*.

The present invention also relates to a vaccine comprising the compositions disclosed herein. Generally, vaccines are prepared as injectables, in the form of aqueous solutions or suspensions. Solid forms which are dissolved or suspended prior to use may also be formulated. Pharmaceutically acceptable carriers, diluents and excipients are generally added that are compatible with the active ingredients and acceptable for pharmaceutical use.

The amount of vaccine sufficient to confer immunity to pathogenic bacteria, viruses, or other microbes is determined by methods well known to those skilled in the art. This quantity will be determined based upon the characteristics of the vaccine recipient and the level of immunity required. Where vaccines are administered by subcutaneous or intramuscular injection, a range of 0.5 to 500 $\mu$g purified protein may be given. As useful in the present invention, such dosages are commonly sufficient to provide about 1 $\mu$g, possibly 10 $\mu$g, even 50 $\mu$g, and as much as 100 $\mu$g, up to 500 $\mu$g of immunogenic protein, or immunogenic polypeptide, or immunogenically active fragments thereof. In addition, more than one such active material may be present in the vaccine. Thus, more than one antigenic structure may be used in formulating the vaccine, or vaccine composition to use in the methods disclosed herein. This may include two or more individually immunogenic proteins or polypeptides, proteins or polypeptides showing immunogenic activity only when in combination, either quantitatively equal in their respective concentrations or formulated to be present in some ratio, either definite or indefinite. Thus, a vaccine composition for use in the processes disclosed herein may include one or more pilus-protein constructs or active fragments thereof, in any proportions selected by the user of the present invention. The exact components, and their respective quantities, making up the vaccines, and vaccine compositions, useful in the methods of the present invention are determined, inter alia, by the nature of the disease to be treated or prevented, the severity of such condition where it already exists, the age, sex, and general health of the recipient, as well the personal and professional experience and inclinations of the researcher and/or clinician utilizing these methods.

Still another aspect of the present invention relates to a method of using one or more antibodies (monoclonal or polyclonal, natural or recombinant, and regardless of how prepared, i.e., by purification from a natural source, or generated by cloning or by direct chemical synthesis), preferably, but not necessarily, specific for one or more antigenic determinants present in the vaccine, or vaccine composition selected for use in the methods of the present invention.

The present invention further relates to a process for treating a disease comprising administering to a patient afflicted with said disease a therapeutically effective amount of a pilus-protein construct disclosed herein. In a preferred embodiment, said disease is an infection, especially wherein said infection is a bacterial infection, most especially wherein said bacterial infection is an infection by *Eschedichia coli*. Such infection may include urinary tract infections.

Where the protein construct of the invention is immunogenic and is to be used as a vaccine, the present invention relates to a process for preventing a disease comprising administering to a patient at risk thereof a prophylactically effective amount of a pilus-protein construct as disclosed herein, preferably wherein the effector portion of said construct comprises an adjuvant or pilus-protein, such as a pilin or adhesin. Such pilus-protein construct may be administered in the form of a composition. In a preferred embodiment, said disease is a urinary tract infection, especially a urinary tract infection caused by an organism of the family enterobacteriaceae, most especially *Escherichia coli*.

In practicing the present invention with pilus-protein constructs, it should be borne in mind that the primary target population is similar to that for a structurally-stabilized complex, such as a complex of FimH and the bacterial chaperone FimC, known commercially as MEDI-516. This population comprises women with uncomplicated urinary tract infection (UTI), several other important clinical settings have been identified in which the prevention of UTI caused by *E. coli* is considered to be important. These include the prevention of asymptomatic bacteriuria in diabetic women (which is a risk factor for more rapid progression to renal failure), the prevention of recurrent UTI in postmenopausal women, the prevention of UTI in patients with impaired bladder emptying due to spinal cord injury, and the prevention of UTI in children with ureterovesicular reflux who are at risk for renal scarring due to repeated UTI.

In accordance with the disclosure herein, it should be kept in mind that certain uses of the pilus protein constructs of the invention do not require a fully structurally stabilized pilus protein but may utilize fragments thereof. Thus, for targeting an construct to the bladder, which exhibits mannosyl residues for binding to adhesins of bacterial, such pilus subunits as FimH contain the active mannose binding domain in about the N-terminal two thirds of their amino acid sequence whereas the donor strand complementary sequence serves to structurally stabilize the pilus protein by interaction with the pilin binding (or C-terminal) portion of molecule. Thus, dsc-strands are of little or no value in stabilizing the mannose binding domains of an adhesin such as FimH. Because of this, where targeting to a mannose-exhibiting tissue is desired, or where the activity contributed to the construct by the pilus-protein does not require domains stabilized by any dsc-strand, the latter can be dispensed with and the required domains of the pilus protein can be linked, covalently or non-covalently, to any of the auxiliary structures disclosed herein. For example, the mannose-binding domain of FimH can be linked to an adjuvant for increased antigenic activity or can be linked to an antibody for increased anti-microbial activity or can be linked to an anticancer agent for increased antitumor activity, such as where said activity, or activities, are to be realized in and around tissues exhibiting mannosyl sites, especially in and around the bladder.

In separate embodiments, such pilus-protein constructs comprise active fragments of a pilus protein linked to some type of polypeptide or polynucleotide. Polypeptides available for such uses include immunoglobulins, such as antibodies and immunologically active fragments thereof. Such active fragments, where they confer immunological activity, may also be linked to adjuvants to enhance such activity. As used herein, the term "active fragment" means a fragment or portion of a pilus protein that serves to confer immunogenic activity on the overall pilus protein construct of which it is a part or where said fragment serves a targeting function to target polypeptides, such as antibodies, or polynucleotides to a specific site, such as where said fragment has mannose-binding activity and serves to target the protein constructs of the invention to a specific tissue location, such as one exhibiting mannosyl residues for binding to said fragment. In a specific embodiment, such fragment comprises the mannosyl-binding domain of FimH.

Further, as used herein, the terms "portion," "segment," and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

What is claimed is:

1. An isolated protein construct comprising a donor-strand complemented- (dsc-) pilus protein linked to an effector wherein said donor-strand complemented- (dsc-) pilus protein comprises a single donor-strand complemented (dsc-) pilus protein, including active fragments thereof, wherein said active fragment is structurally-stabilized by the presence of a donor strand and wherein said donor-strand complemented- (dsc-) pilus protein is not attached to a bacterial cell and wherein said effector does not comprise all or part of either a bacterial pilus-protein or bacterial chaperone.

2. The isolated protein construct of claim 1 wherein said pilus-protein is a protein that in living bacterial cells acts as a substrate for assembly into a bacterial surface structure by the usher-chaperone pathway.

3. The isolated protein construct of claim 1 wherein said pilus-protein is a pilin selected from the group consisting of FimH, FimA, FimG, FimF, PapG, PapA, PapE, PapF, and PapK.

4. The isolated protein construct of claim 1 wherein said pilus-protein is an adhesin selected from the group consisting of FimH and PapG.

5. The isolated protein construct of claim 1 wherein said effector is attached to the dsc-pilus protein by the donor strand (ds).

6. The isolated protein construct of claim 5 wherein said donor strand is covalently linked to at least one of said pilus-protein or said effector.

7. The isolated protein construct of claim 6 wherein said donor strand is covalently linked to said pilus-protein but not to said effector.

8. The isolated protein construct of claim 6 wherein said donor strand is covalently linked to said effector but not to said pilus-protein.

9. The isolated protein construct of claim 6 wherein said donor strand is covalently linked to both said pilus-protein and said effector.

10. The isolated protein construct of claim 6 wherein said donor strand is non-covalently linked to said pilus-protein and to said effector.

11. The isolated protein construct of claim 5 wherein said pilus-protein is a protein that in living bacterial cells acts as a substrate for assembly into a bacterial surface structure by the usher-chaperone pathway.

12. The isolated protein construct of claim 5 wherein said pilus-protein is a pilin selected from the group consisting of FimH, FimA, FimG, FimF, PapG, PapA, PapE, PapF, and PapK.

13. The isolated protein construct of claim 5 wherein said pilus-protein is an adhesin selected from the group consisting of FimH and PapG.

14. The isolated protein construct of claim 1 wherein said effector is an immunoglobulin.

15. The isolated protein construct of claim 14 wherein said immunoglobulin comprises at least one heavy and one light chain variable region of an antibody.

16. The isolated protein construct of claim 14 wherein said immunoglobulin is an antibody.

17. The isolated protein construct of claim 16 wherein said antibody has specificity for at least one antigenic determinant of a microorganism.

18. The isolated protein construct of claim 17 wherein said microorganism is selected from the group consisting of viruses, bacteria, fungi and protozoans.

19. The isolated protein construct of claim 18 wherein said microorganism is a bacterium.

20. The isolated protein construct of claim 19 wherein said bacterium is *Escheiichia coil.*

21. A composition comprising the protein construct of claim 14 wherein said protein is suspended in a pharmacologically acceptable carrier.

22. The isolated protein construct of claim 1 wherein said effector comprises an adjuvant.

23. The protein construct of claim 1 wherein said effector comprises a chemotherapeutic agent.

24. The protein construct of claim 23 wherein said chemotherapeutic agent is an anticancer agent.

25. The protein construct of claim 16 wherein said antibody is VITAXIN®.

* * * * *